United States Patent
Hu

(10) Patent No.: US 10,792,370 B2
(45) Date of Patent: Oct. 6, 2020

(54) ANTIBODY-DRUG CONJUGATE

(71) Applicant: SHANGHAI MIRACOGEN INC, Shanghai (CN)

(72) Inventor: Chaohong Hu, Shanghai (CN)

(73) Assignee: SHANGHAI MIRACOGEN INC, Shanghai (CN)

( * ) Notice: Subject to any disclaimer, the term of this patent is extended or adjusted under 35 U.S.C. 154(b) by 225 days.

(21) Appl. No.: 15/550,995

(22) PCT Filed: Feb. 16, 2016

(86) PCT No.: PCT/CN2016/073844
§ 371 (c)(1),
(2) Date: Aug. 14, 2017

(87) PCT Pub. No.: WO2016/131409
PCT Pub. Date: Aug. 25, 2016

(65) Prior Publication Data
US 2018/0036423 A1 Feb. 8, 2018

(30) Foreign Application Priority Data
Feb. 17, 2015 (CN) .......................... 2015 1 0085038

(51) Int. Cl.
| | | |
|---|---|---|
| *A61K 47/68* | (2017.01) | |
| *A61P 35/00* | (2006.01) | |
| *A61K 39/00* | (2006.01) | |
| *A61P 9/10* | (2006.01) | |
| *C07K 16/28* | (2006.01) | |
| *A61K 38/18* | (2006.01) | |
| *G01N 30/88* | (2006.01) | |
| *G01N 30/02* | (2006.01) | |

(52) U.S. Cl.
CPC ...... *A61K 47/6811* (2017.08); *A61K 38/1808* (2013.01); *A61K 39/0011* (2013.01); *A61K 39/001104* (2018.08); *A61K 47/6803* (2017.08); *A61K 47/6851* (2017.08); *A61P 9/10* (2018.01); *A61P 35/00* (2018.01); *C07K 16/2863* (2013.01); *A61K 2039/505* (2013.01); *C07K 2317/24* (2013.01); *C07K 2317/73* (2013.01); *C07K 2317/76* (2013.01); *G01N 2030/027* (2013.01); *G01N 2030/8809* (2013.01)

(58) Field of Classification Search
CPC ............ A61K 47/6889; A61K 47/6849; A61K 38/1808; A61K 39/001104
See application file for complete search history.

(56) References Cited

U.S. PATENT DOCUMENTS 7,960,516 B2 * 6/2011 Matheus .......... A61K 39/39591
530/387.3

FOREIGN PATENT DOCUMENTS

| CN | 103772504 | 5/2014 | |
|---|---|---|---|
| WO | WO 2014152199 | 9/2014 | |
| WO | WO-2015000062 A1 * | 1/2015 | ............. A61K 47/50 |

OTHER PUBLICATIONS

Prabhakar et al, Cancer Research, 2013, vol. 73, pp. 2412-2417 (Year: 2013).*
Yoo and Park, Journal of Controlled Release, 2001, vol. 70, pp. 63-70 (Year: 2001).*
Brand et al (Cancer Biology & Therapy, 2011, vol. 11, pp. 777-792) (Year: 2011).*
Chung et al (New England Journal of Medicine, 2008, vol. 358, pp. 1109-1117) (Year: 2008).*
Chari et al (Angewandte Chemie, 2014, vol. 53, pp. 3796-3827) (Year: 2014).*
Lievre et al (Cancer Research, 2006, vol. 66, pp. 3992-3995) (Year: 2006).*
DiNicolantonio et al (Journal of Clinical Oncology, 2008, vol. 26, pp. 5705-5712) (Year: 2008).*
EPO Translation of CN103772504, downloaded from the Web on Mar. 16, 2019 (Year: 2019).*
Goldmacher and Kovtun (Therapeutic Delivery, 2011, vol. 2, pp. 397-416) (Year: 2011).*
Polson et al (Cancer Research, 2009, vol. 69, pp. 2358-2364) (Year: 2009).*
Doronina et al (Cancer Research, 2006, vol. 17, pp. 114-124) (Year: 2006).*
Dorywalska et al (Bioconjugate Chemistry, Feb. 2, 2015, vol. 26, pp. 650-659) (Year: 2015).*
Erickson et al (Molecular Cancer Therapeutics, 2012, vol. 11, pp. 1133-1142) (Year: 2012).*

* cited by examiner

*Primary Examiner* — Karen A. Canella
(74) *Attorney, Agent, or Firm* — Seed IP Law Group LLP

(57) ABSTRACT

The present invention relates to an antibody-drug conjugate, in particular, to an antibody-drug conjugate targeting an epidermal growth factor receptor. The present invention also relates to a composition comprising the antibody-drug conjugate, and use of the antibody-drug conjugate in manufacture of a medicament for the prophylaxis and/or treatment of a disease associated with epidermal growth factor receptor, in particular in manufacture of a medicament for prophylaxis and/or treatment of colon cancer, rectal cancer, head and neck cancer, lung cancer, ovarian cancer, cervical cancer, bladder cancer and esophageal cancer. The antibody-drug conjugate of the invention has a good inhibition activity on tumor cell growth both in vivo and in vitro, and has low toxicity, and thus has a good application prospect.

23 Claims, 7 Drawing Sheets
Specification includes a Sequence Listing.

ANTIBODY-DRUG CONJUGATE

CROSS-REFERENCE TO RELATED APPLICATIONS

This application is a § 371 national phase of International Application No. PCT/CN2016/073844, filed on Feb. 16, 2016, which claims the benefit of Chinese Application No. 201510085038.8, filed on Feb. 17, 2015, which applications are incorporated by reference herein.

TECHNICAL FIELD

The present invention relates to an antibody-drug conjugate, in particular to an antibody-drug conjugate in which said antibody is an anti-epidermal growth factor receptor antibody. The present invention also relates to a composition comprising the antibody-drug conjugate, and to a pharmaceutical use of the antibody-drug conjugate.

BACKGROUND ART

Epidermal growth factor receptor (Epidermal Growth Factor Receptor, EGFR, also known as HER1, c-ErbB1) is a cell surface receptor of epidermal growth factor family, is a transmembrane glycoprotein composed of 1186 amino acid residues, and has a molecular weight of 170 kD (Jorissen R N, Walker F, Pouliot N, et al. Epidermal growth factor receptor: mechanisms of activation and signaling. Exp Cell Res, 2003; 284:31-53). EGFR belongs to type I tyrosine kinase receptor subfamily ErbB (ErbB 1-4) and has tyrosine kinase activity. EGFR is stably expressed in many epithelial tissues, including the skin and hair follicles. Abnormal expression of epidermal growth factor receptor or activation caused by receptor mutation may lead to carcinogenesis. There are many solid tumors where over expression of epidermal growth factor receptor are found, such as colorectal cancer, head-neck cancer, lung cancer, ovarian cancer, cervical cancer, bladder cancer and esophageal cancer (Olayioye M A, Neve R M, Lane H A, et al. The EerbB Signaling network: receptor heterodimerzation in development and cancer. The EMBO J, 2000; 19:3159-3167). Growth factors such as transforming growth factor $\alpha$ and epidermal growth factor are endogenous ligands for EGFR. These ligands bind to epidermal growth factor receptor and activate intracellular tyrosine protein kinase activity, initiate a lot of downstream signal transduction pathways, thereby regulating growth and differentiation of normal cells, enhancing invasiveness of tumor cells, promoting angiogenesis and inhibiting apoptosis of tumor cells (Ciardiello F, Tortora G. A novel approach in the treatment of cancer: targeting the epidermal growth factor receptor. Clin Cancer Res, 2001; 7:2958-2970). Epidermal growth factor receptor overexpression in tumor and its important roles in the growth and differentiation of tumor cells make epidermal growth factor receptor a promising target for tumor therapy.

At present, there are two anti-epidermal growth factor receptor antibodies in the market, one is human-mouse chimeric antibody C225 antibody (Erbitux or Cetuximab, ImClone Company (now Eli Lilly Company)), which has a specific binding affinity to epidermal growth factor receptor, can block the binding between a ligand such as EGF or TGFα and a epidermal growth factor receptor, inhibit its phosphorylation and downstream signal transduction, thereby inhibiting tumor cell growth, inducing apoptosis, reducing production of matrix metalloproteinases and vascular endothelial growth factor. The FDA of the United States approved the use of Erbitux for treatment of colorectal cancer in 2004, for treatment of head and neck cancer in 2006, and for other cancer indications in more clinical trials now. Clinically, the overall response rate (ORR) of the combination of Erbitux and irinotecan in treatment of colorectal cancer is 23%, and the ORR of the combination of Erbitux and chemotherapy drug such as fluoropyrimidine in treatment of head and neck cancer is 13%-30%. Because of being a human-mouse chimeric antibody, Erbitux induced an anti-therapeutic antibody response in 3.7% of the patients in the clinical trial.

Another anti-epidermal growth factor receptor antibody is panitumumab (Vectibix, panitumumab, Amgen), which is a fully humanized monoclonal antibody prepared by using transgenic mouse technology, and is free of mouse original protein sequence. The antibody targets epidermal growth factor receptor (EGFR), and was approved by the FDA in September 2006, used in combination with fluoropyrimidine, Oxaliplatin and Irinotecan or for treatment of EGFR positive metastatic colorectal cancer after chemotherapy. In 2006, FDA approved its monotherapy for the treatment of metastatic colorectal cancer (mCRC) with chemotherapy tolerance. However, panitumumab is an IgG2 subtype antibody, and compared with IgG1, IgG2 exhibits significantly decreased biological activities such as CDC activity and ADCC activity; in addition, IgG2 subtype antibodies usually have poor stability. These may be the main reasons that fully humanized antibody panitumumab shows no obvious advantages in clinical effects in comparison with chimeric antibody Erbitux. The overall survival rate (OR) in clinical treatment of colorectal cancer was merely 8% and the progression free survival was only extended by 3.6 months.

At present, large amount of clinical data showed that Erbitux and panitumumab had therapeutic effects only on wild type KRAS (KRAS wild type) with expression of EGFR, but had no tumor growth inhibitory activity to KRAS mutants. Therefore, the Guidelines published by the American Society of Clinical Oncology explicitly point out that anti-EGFR monoclonal antibody drugs are only applicable to KRAS wild type colorectal cancer patients (Allegra C J, Jessup J M, Somerield M R, Hamilton S R, Hammond E H, Hayes D F, et al. American Society of Clinical Oncology provisional clinical opinion: testing for KRAS gene mutations in patients with metastatic colorectal carcinoma to predict response to anti-epidermal growth factor monoclonal antibody therapy. J. Clin Oncol. 2009; 27:2091-2096; Bardelli A, Siena S. Molecular mechanisms of resistance to cetuximab and panitumumab in Colorectal, cancer., J, Clin, Oncol. 2010; 28:1254-1261).

Therefore, it is in need in the art to have humanized anti-epidermal growth factor receptor antibody drugs with biological activity, especially antibody drugs, such as antibody-drug conjugates, with curative effects to KRAS mutants, so as to further improve therapeutic efficacy and reduce side effects.

In recent years, the rapid development of antibody-drug conjugates (ADC) has become one of the most advanced biopharmaceutical technologies in recent years due to the lead of monoclonal antibody cancer drugs.

An antibody drug conjugate usually consists of three parts:
1. monoclonal antibody with specific binding to a target;
2. small molecule chemical drug with cytotoxicity;
3. linker that links the small molecule drug and the monoclonal antibody.

An antibody-drug conjugate kills tumor cells by utilizing the target specificity of the monoclonal antibody and the cytotoxicity of the chemical drug. Its mechanism of action is: (1) the antibody-drug conjugate specifically binds to a target antigen expressed on a tumor cell surface by the monoclonal antibody; (2) the complex of the antibody drug conjugate and the target antigen enters the cell via endocytosis mediated by the target antigen; (3) the antibody-drug conjugate degrades in the cell and releases the cytotoxic chemical drug; (4) the cytotoxic chemical drug kills the tumor cell.

Although the mechanism of antibody drug conjugate appears straightforward, it is highly complex and unpredictable whether an antibody drug conjugate becomes a safe and effective drug depending on a variety of factors, such as:

1) characteristics of target: whether a target antigen can be internalized or not, the expression level of the target antigen, differentials of expression level of target antigen between cancer cells and normal cells, and whether the target antigen has a extracellular domain (ECD) that is soluble in blood;

2) characteristics of monoclonal antibody: specificity of the monoclonal antibody to the target antigen (preferably no cross-reaction with other proteins), stability of the monoclonal antibody, and whether the complex of the monoclonal antibody and the target can be endocytosed into the cell;

3) characteristics of small molecule drug: potency of the cytotoxicity of the small molecule drug, stability thereof in blood, and toxicity of the in vivo metabolites of the ADC containing the small molecule drug;

4) characteristics of linker: whether the linker is cleavable or non-cleavable, and stability of the linker in blood;

5) ADC characteristics: whether the complex of ADC and target antigen can be internalized or not, stability of ADC in blood, linker used and number of chemical drugs conjugated to the ADC, the balance between cancer killing activity of ADC and its toxicity.

Therefore, the development of ADC drugs requires substantial amount of experimental exploration and confirmation in the preclinical and clinical studies. Its safety and efficacy are hardly predictable.

CONTENTS OF THE INVENTION

The inventors of the present invention have prepared an anti-epidermal growth factor receptor antibody-drug conjugate through a large number of experiments and creative work, and confirmed that it has good biological activities, thereby completing the present invention.

A first aspect of the invention relates to an antibody-drug conjugate, a pharmaceutically acceptable salt thereof, a solvate thereof or a solvate of the salt, comprising an anti-epidermal growth factor receptor antibody covalently linked to a cytotoxic agent.

In one embodiment of the invention, the anti-epidermal growth factor receptor antibody comprises a heavy chain and a light chain, wherein the heavy chain has a variable region comprising CDR1, CDR2 and CDR3 having sequences as shown in SEQ ID NOs: 5 to 7 or mutants thereof, and the light chain has a variable region comprising CDR1, CDR2 and CDR3 having sequences as shown in SEQ ID NOs: 12 to 14 or mutants thereof.

In one embodiment of the invention, the CDR1, CDR2 and CDR3 of the variable region of the light chain of said anti-epidermal growth factor receptor antibody respectively comprise sequences as shown in SEQ ID NOs: 12 to 14, or comprise sequences with identity of greater than 70%, such as greater than 75%, 80%, 85%, 90%, 91%, 92%, 93%, 94%, 95%, 96%, 97% 98%, or 99% to sequences as shown in SEQ ID NOs: 12 to 14, for example, sequences having 3, 2 or 1 mutations, deletions or addition of amino acids.

In one embodiment of the invention, the CDR1, CDR2 and CDR3 of the variable region of the heavy chain of said anti-epidermal growth factor receptor antibody respectively comprise sequences as shown in SEQ ID NOs: 5 to 7, or comprise sequences with identity of greater than 70%, such as greater than 75%, 80%, 85%, 90%, 91%, 92%, 93%, 94%, 95%, 96%, 97% 98%, or 99% to the sequences as shown in SEQ ID NOs: 5 to 7, for example, sequences having 3, 2 or 1 mutations, deletions or addition of amino acids.

In one embodiment of the invention, FR1, FR2, FR3, FR4 of the variable region of the heavy chain of said anti-epidermal growth factor receptor antibody respectively comprise sequences as shown in SEQ ID NOs: 8 to 11 or mutants thereof.

In one embodiment of the invention, FR1, FR2, FR3, FR4 of the variable region of the heavy chain of said anti-epidermal growth factor receptor antibody respectively comprise sequences as shown in SEQ ID NOs: 8 to 11, or comprise sequences with identity of greater than 70%, for example, greater than 75%, 80%, 85%, 90%, 91%, 92%, 93%, 94%, 95%, 96%, 97%, 98%, or 99% to the above sequences.

In one embodiment of the invention, FR1, FR2, FR3, FR4 of the variable region of the light chain of said anti-epidermal growth factor receptor antibody respectively comprise sequences as shown in SEQ ID NOs: 15 to 18, or mutants thereof.

In one embodiment of the invention, FR1, FR2, FR3, FR4 of the variable region of the light chain of said anti-epidermal growth factor receptor antibody respectively comprise sequences as shown in SEQ ID NOs: 15 to 18, or comprise sequences with identity of greater than 70%, for example, greater than 75%, 80%, 85%, 90%, 91%, 92%, 93%, 94%, 95%, 96%, 97%, 98%, or 99% to the above sequences.

In one embodiment of the invention, the variable region of the heavy chain of the anti-epidermal growth factor receptor antibody has a sequence as shown in SEQ ID NO: 1.

In one embodiment of the invention, the variable region of the light chain of the anti-epidermal growth factor receptor antibody has a sequence as shown in SEQ ID NO: 2.

In one embodiment of the invention, the heavy chain of the anti-epidermal growth factor receptor antibody has a constant region selected from the group consisting of a human IgG constant region, a human IgM constant region, a human IgA constant region, a human IgD constant region and a mutant thereof.

In one embodiment of the invention, the IgG is selected from IgG1, IgG2, IgG3 and IgG4.

In one embodiment of the invention, constant region of the heavy chain of the anti-epidermal growth factor receptor antibody comprises an amino acid sequence as shown in SEQ ID NO: 3, or comprises a sequence with identity of greater than 70%, for example, greater than 75%, 80%, 85%, 90%, 91%, 92%, 93%, 94%, 95%, 96%, 97%, 98%, or 99% to the sequence as shown in SEQ ID NO: 3.

In one embodiment of the invention, constant region of the light chain of the anti-epidermal growth factor receptor antibody is a human lambda constant region, a human kappa constant region, or a mutant thereof.

In one embodiment of the invention, constant region of the light chain of the anti-epidermal growth factor receptor antibody comprises an amino acid sequence as set forth in SEQ ID NO: 4, or comprises a sequence with identity of greater than 70%, for example, greater than 75%, 80%, 85%, 90%, 91%, 92%, 93%, 94%, 95%, 96%, 97%, 98%, or 99% of the sequence as shown in SEQ ID NO: 4.

In one embodiment of the present invention, the antibody-drug conjugate, the pharmaceutically acceptable salt thereof, the solvate thereof or the solvate of said salt, has a structure represented by Formula I, $$Ab\text{-}(L\text{-}D)_p$$ Formula □

Wherein:
Ab represents the anti-epidermal growth factor receptor antibody;
L represents a linker;
D represents the cytotoxic agent;
p represents 1-8, for example 2-6, e.g. 3-5.

In one embodiment of the invention, said cytotoxic agent is selected from the group consisting of chemotherapeutic agents, toxins (e.g., bacterial, fungal, plant, or animal-derived enzymatically active toxins or fragments thereof), radioisotopes, cytokines, antibiotics, enzymes, nanoparticles and biologically active peptides.

In one embodiment of the invention, said cytotoxic agent is selected from the group consisting of Monomethyl auristatin E (MMAE), Monomethyl auristatin F (MMAF), maytansinoid alkaloids (e.g., Maytansine DM1, Maytansine DM4), Calicheamicin, duocarmycin MGBA, doxorubicin, ricin, diphtheria toxin and other toxins, I131, interleukins, tumor necrosis factors, chemokines and nanoparticles.

In one embodiment of the invention, said cytotoxic agent is MMAE.

In one embodiment of the invention, said linker is cleavable or non-cleavable.

In one embodiment of the present invention, the linker is selected from the group consisting of 6-maleimidocaproyl (MC), maleimidopropionyl (MP), valine-citrulline (val-cit), alanine-phenylalanine (ala-phe), p-aminobenzyloxycarbonyl (PAB), N-succinimidyl 4-(2-pyridylthio)valerate (SPP), N-succinimidyl 4-(N-maleimidomethyl)-cyclohexane-1-carboxylate (SMCC), N-succinimidyl (4-iodo-acetyl) aminobenzoate (SIAB), and 6-maleimidocaproyl-valine-citrulline-p-aminobenzyloxycarbonyl (MC-vc-PAB).

In one embodiment of the present invention, said linker is 6-maleimidocaproyl-valine-citrulline-p-aminobenzyloxycarbonyl (MC-vc-PAB).

In one embodiment of the present invention, the L-D in formula I is vc-MMAE, and the structure is as follows:

Wherein, Ab represents the anti-epidermal growth factor receptor antibody, p is 1-8, e.g. 2-6, e.g. 3-5.

The second aspect of the present invention relates to a composition (e.g., a pharmaceutical composition) comprising the antibody-drug conjugate, the pharmaceutically acceptable salt thereof, the solvate thereof or the solvate of the salt according to any one of items of the first aspect of the present invention, optionally, further comprising at least one pharmaceutically acceptable carrier, diluent or excipient.

In one embodiment of the present invention, the composition further comprises a known chemotherapeutic agent for the treatment of a tumor, such as Adriamycin, cyclophosphamide and taxane [Taxol and Taxotere], Xeloda, Gemzar, Navelbine, Tamoxifen, aromatase inhibitors (Ruining, Fulong, Arnoldin), 5-FU plus folinic acid, camptosar, oxaliplatin, cisplatin, carboplatin, estramustine, Novantrone, prednisone, vincristine (Oncovin), etc., or a combination thereof.

The present invention also relates to a use of the antibody-drug conjugate, the pharmaceutically acceptable salt thereof, the solvate thereof or the solvate of the salt according to the first aspect of the invention in manufacture of a medicament for prophylaxis and/or treatment of a disease associated with epidermal growth factor receptor (EGFR).

In one embodiment of the invention, the disease associated with epidermal growth factor receptor (EGFR) is a tumor associated with EGFR, such as a tumor associated with overexpression of EGFR, e.g., selected from colon cancer, rectal cancer, head and neck cancer, lung cancer, ovarian cancer, cervical cancer, bladder cancer, esophageal cancer, breast cancer, kidney cancer, prostate cancer, gastric cancer, pancreatic cancer and brain glioma.

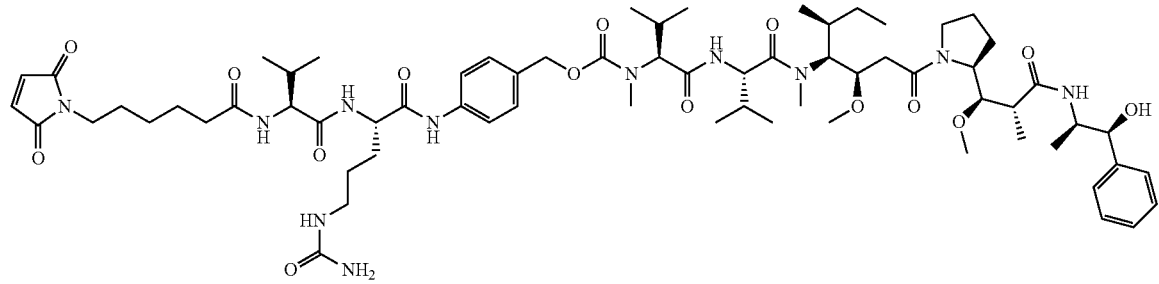

In a particular embodiment of the invention, the antibody-drug conjugate, the pharmaceutically acceptable salt thereof, the solvate thereof or the solvate of said salt is represented by the following formula:

In one embodiment of the invention, the tumor is a tumor with KRAS gene mutation, e.g., selected from colon cancer, rectal cancer, lung cancer or pancreatic cancer with KRAS gene mutation.

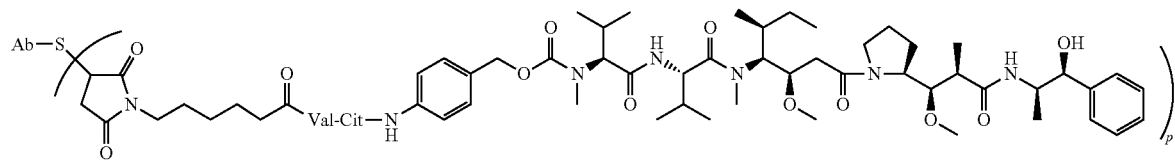

In one embodiment of the invention, the tumor is a tumor with BRAF gene mutation, e.g., selected from colon cancer, rectal cancer, and lung cancer with BRAF gene mutation.

The invention also relates to a use of the antibody-drug conjugate, the pharmaceutically acceptable salt thereof, the solvate thereof or the solvate of the salt according to the first aspect of the present invention in manufacture of a medicament for inhibiting tumor angiogenesis, delaying tumor progression, inhibiting tumor growth, or inhibiting tumor cell proliferation.

In one embodiment of the invention, the tumor is selected from colon cancer, rectal cancer, head and neck cancer, lung cancer, ovarian cancer, cervical cancer, bladder cancer, esophageal cancer, breast cancer, renal cancer, prostate cancer, gastric cancer, pancreatic cancer and brain glioma.

In one embodiment of the invention, the tumor is a tumor with KRAS gene mutation, e.g., selected from colon cancer, rectal cancer, lung cancer or pancreatic cancer with KRAS gene mutation.

In one embodiment of the invention, wherein the tumor is a tumor with BRAF gene mutation, e.g., selected from colon cancer, rectal cancer, and lung cancer with BRAF gene mutation.

The invention also relates to a method for prophylaxis and/or treatment of a disease associated with epidermal growth factor receptor (EGFR), wherein the method comprising a step of administering to a subject in need a prophylactically and/or therapeutically effective amount of the antibody-drug conjugate, the pharmaceutically acceptable salt thereof, the solvate thereof or the solvate of the salt according to the first aspect of the invention.

In one embodiment of the invention, the disease associated with epidermal growth factor receptor (EGFR) is a tumor associated with EGFR, such as a tumor associated with overexpression of EGFR, e.g., selected from colon cancer, rectal cancer, head and neck cancer, lung cancer, ovarian cancer, cervical cancer, bladder cancer, esophageal cancer, breast cancer, renal cancer, prostate cancer, gastric cancer, pancreatic cancer and brain glioma.

In one embodiment of the invention, the tumor is a tumor with KRAS gene mutation, for example, colon cancer, colorectal cancer, lung cancer or pancreatic cancer with KRAS gene mutation.

In one embodiment of the invention, the tumor is a tumor with BRAF gene mutation, for example colon cancer, rectal cancer and lung cancer with BRAF gene mutation.

The invention also relates to a method for inhibiting tumor angiogenesis, delaying tumor progression, inhibiting tumor growth, or inhibiting tumor cell proliferation, wherein the method comprising a step of administering to a subject in need a prophylactically and/or therapeutically effective amount of the antibody-drug conjugate, the pharmaceutically acceptable salt thereof, the solvate thereof or the solvate of the salt according to the first aspect of the invention.

In one embodiment of the invention, wherein the tumor is selected from colon cancer, rectal cancer, head and neck cancer, lung cancer, ovarian cancer, cervical cancer, bladder cancer, esophageal cancer, breast cancer, renal cancer, prostate cancer, gastric cancer, pancreatic cancer and brain glioma.

In one embodiment of the invention, the tumor is a tumor with KRAS gene mutation, for example, colon cancer, colorectal cancer, lung cancer or pancreatic cancer with KRAS gene mutation.

In one embodiment of the invention, the tumor is a tumor with BRAF gene mutation, for example colon cancer, rectal cancer and lung cancer with BRAF gene mutation.

The invention also relates to the antibody-drug conjugate, the pharmaceutically acceptable salt thereof, the solvate thereof or the solvate of the salt according to the first aspect of the invention, which is used for prophylaxis and/or treatment of a disease associated with epidermal growth factor receptor (EGFR).

In one embodiment of the invention, the disease associated with epidermal growth factor receptor (EGFR) is a tumor associated with EGFR, such as a tumor associated with overexpression of EGFR, e.g., selected from colon cancer, rectal cancer, head and neck cancer, lung cancer, ovarian cancer, cervical cancer, bladder cancer, esophageal cancer, breast cancer, renal cancer, prostate cancer, gastric cancer, pancreatic cancer and brain glioma.

In one embodiment of the invention, the tumor is a tumor with KRAS gene mutation, for example, colon cancer, colorectal cancer, lung cancer or pancreatic cancer with KRAS gene mutation.

In one embodiment of the invention, the tumor is a tumor with BRAF gene mutation, for example colon cancer, rectal cancer and lung cancer with BRAF gene mutation.

The invention also relates to the antibody-drug conjugate, the pharmaceutically acceptable salt thereof, the solvate thereof or the solvate of the salt according to the first aspect of the invention, which is used for inhibiting tumor angiogenesis, delaying tumor progression, inhibiting tumor growth, or inhibiting tumor cell proliferation.

In one embodiment of the invention, the tumor is selected from colon cancer, rectal cancer, head and neck cancer, lung cancer, ovarian cancer, cervical cancer, bladder cancer, esophageal cancer, breast cancer, renal cancer, prostate cancer, gastric cancer, pancreatic cancer and brain glioma.

In one embodiment of the invention, the tumor is a tumor with KRAS gene mutation, for example, colon cancer, colorectal cancer, lung cancer or pancreatic cancer with KRAS gene mutation.

In one embodiment of the invention, the tumor is a tumor with BRAF gene mutation, for example colon cancer, rectal cancer and lung cancer with BRAF gene mutation.

The anti-epidermal growth factor receptor antibody-drug conjugate, the pharmaceutically acceptable salt thereof, the solvate thereof or the solvate of the salt according to the present invention has a good inhibition activity on tumor cell growth in vivo and in vitro, especially obvious inhibition activity on tumor growth of tumor cells with middle level or low level expression of EGFR, as well as has low cytotoxicity; more specifically, the anti-EGFR antibody-drug conjugate, the pharmaceutically acceptable salt thereof, the solvate thereof or the solvate of the salt according to the present invention also has good curative effects on tumors with KRAS gene mutation or BRAF gene mutation, so that it has good application prospects.

The present invention is further described as follows:

In the present invention, the scientific and technical terms used herein have the same meaning as commonly understood by one of ordinary skill in the art, unless otherwise indicated. Also, the terms and laboratory procedures relevant to chemistry of proteins and nucleic acids, molecular biology, cell and tissue culture, microbiology, immunology are all terms and conventional steps that are widely used in the corresponding fields. Meanwhile, for the purpose of better understanding the present invention, definitions and explanations of related terms are provided below.

In the present invention, the term "antibody" refers to an immunoglobulin molecule that is typically composed of two pairs of identical polypeptide chains (each having a "light" (L) chain and a "heavy" (H) chain). The light chain of antibody can be divided into two types: κ and λ. The heavy chain can be divided into five types: μ, δ, γ, α or ε, and the antibody can be therefore divided according to different types of heavy chain into five types: IgM, IgD, IgG, IgA and IgE. Within the light and heavy chains, the variable and constant regions are linked by a "J" region of about 12 or more amino acids, and the heavy chain further comprises a "D" region of about 3 or more amino acids. Each heavy chain consists of a heavy chain variable region ($V_H$) and a heavy chain constant region ($C_H$). The heavy chain constant region consists of three domains ($C_H1$, $C_H2$ and $C_H3$). Each light chain consists of a light chain variable region ($V_L$) and a light chain constant region ($C_L$). The light chain constant region consists of one domain $C_L$. The constant regions of antibody may mediate the binding of immunoglobulin to a host tissue or factor, including various cells (e.g., effector cells) of the immune system and component C1q of the complement system. The $V_H$ and $V_L$ regions can also be subdivided into regions with high variability (called complementarity determining regions (CDRs)) among which more conserved regions known as framework regions (FR) are scattered. Each of $V_H$ and $V_L$ consists of three CDRs and 4 FRs arranged in the following order: FR1, CDR1, FR2, CDR2, FR3, CDR3, FR4 from the amino terminus to the carboxy terminus. The variable regions ($V_H$ and $V_L$) of each heavy chain/light chain pair form antibody binding sites, respectively. The distribution of amino acids to regions or domains follows the definitions of Kabat Sequences of Proteins of Immunological Interest (National Institutes of Health, Bethesda, Md. (1987 and 1991)), or Chothia & Lesk (1987) J. Mol. Biol. 196: 901-917; definition of Chothia et al. (1989) Nature 342: 878-883. The term "antibody" is not limited by any particular method of producing an antibody. For example, it comprises, in particular, recombinant antibodies, monoclonal antibodies, and polyclonal antibodies. The antibodies may be different types of antibodies, e.g., IgG (e.g., IgG1, IgG2, IgG3 or IgG4 subtype), IgA1, IgA2, IgD, IgE or IgM antibodies.

In the present invention, the IgG heavy chain constant region comprises IgG1, IgG2, IgG3 or IgG4. In an embodiment of the invention, the IgG heavy chain constant region is an IgG1 type.

In the present invention, the κ light chain constant region comprises various allotypes, such as Km1, Km1, 2 or Km3.

About Amino Acid Sequence of Antibody

In an embodiment of the invention, the heavy chain variable region amino acid sequence of the anti-epidermal growth factor receptor antibody is SEQ ID NO: 1. In an embodiment of the invention, the light chain variable region amino acid sequence of the anti-epidermal growth factor receptor antibody is SEQ ID NO: 2.

In another aspect, the antibody heavy chain variable region amino acid sequence of the invention is at least 70%, preferably at least 75%, preferably at least 80%, preferably 85% more preferably at least 90%, and most preferably at least 95% identical to the sequence of SEQ ID NO: 1.

In another aspect, the antibody light chain variable region amino acid sequence of the invention is at least 70%, preferably at least 75%, preferably at least 80%, preferably at least 85%, more preferably at least 90%, and most preferably at least 95% identical to the sequence identity of SEQ ID NO: 2.

In an embodiment of the invention, the amino acid sequences of CDRs of the heavy and light chain variable regions of epidermal growth factor receptor antibody are determined as follows:

The amino acid sequences of CDR1, CDR2 and CDR3 of heavy chain are SEQ ID NO: 5 to 7, respectively; the amino acid sequences of CDR1, CDR2 and CDR3 of light chain are SEQ ID NO: 12 to 14, respectively.

In another aspect, the amino acid sequences contained in the CDRs of heavy chains of the anti-epidermal growth factor receptor antibody may have one or more mutations or additions or deletions of amino acids in SEQ ID NOs: 5 to 7. Preferably, the amino acids for the mutations, additions or deletions are not more than 3 amino acids. More preferably, the amino acids for the mutations, additions or deletions are not more than 2 amino acids. Most preferably, the amino acids for the mutations, additions or deletions are not more than 1 amino acid.

In another aspect, the amino acid sequences contained in the CDRs of light chains of the anti-epidermal growth factor receptor antibody may have one or more mutations or additions or deletions of amino acids in SEQ ID NOs: 12 to 14. Preferably, the amino acids for the mutations, additions or deletions are not more than 3 amino acids. More preferably, the amino acids for the mutations, additions or deletions are not more than 2 amino acids. Most preferably, the amino acids for the mutations, additions or deletions are not more than 1 amino acid.

In an embodiment of the invention, the amino acid sequences of FRs of the heavy and light chain variable regions of the epidermal growth factor receptor antibody are determined as follows:

The sequences of the heavy chain variable regions FR1, FR2, FR3 and FR4 are SEQ ID NO: 8 to 11, respectively. The sequences of the light chain variable regions FR1, FR2, FR3 and FR4 are SEQ ID NO: 15 to 18, respectively.

On the other hand, the amino acid sequences of heavy or light chain variable regions FRs of the anti-epidermal growth factor receptor antibody may have one or more mutations or additions or deletions of amino acids in SEQ ID NOs: 8 to 11 and SEQ ID Nos: 15 to 18. Preferably, the amino acids for the mutations, additions or deletions are not more than 3 amino acids. More preferably, the amino acids for the mutations, additions or deletions are not more than 2 amino acids. Most preferably, the amino acids for the mutations, additions or deletions are not more than 1 amino acid.

The mutants with the above mutations, additions or deletions in antibody or CDR regions or framework regions still retain the ability of specific binding to EGFR.

In an embodiment of the invention, the anti-epidermal growth factor receptor antibody heavy chain constant region amino acid sequence is SEQ ID NO: 3. In an embodiment of the invention, the anti-epidermal growth factor receptor antibody light chain constant region amino acid sequence is SEQ ID NO: 4.

In another aspect, the amino acid sequence of the antibody heavy chain constant region of the invention is at least 70%, preferably at least 75%, preferably at least 80%, preferably at least 85%, more preferably at least 90%, most preferably at least 95%, such as 96%, 97%, 98%, 99% identical to SEQ ID NO: 3.

In another aspect, the amino acid sequence of the antibody light chain constant region of the invention is at least 70%, preferably at least 75%, preferably at least 80%, preferably at least 85%, more preferably at least 90%, most preferably at least 95%, such as 96%, 97%, 98%, 99% identical to SEQ ID NO: 4.

The monoclonal antibody variants of the present invention can be obtained by conventional genetic engineering methods. Those skilled in the art are fully aware of the methods of transforming DNA molecules using nucleic acid mutations. In addition, nucleic acid molecules encoding heavy and light chain variants can also be obtained by chemical synthesis.

In the present invention, the algorithms for determining the percentage of sequence identity (homology) and sequence similarity are, for example, BLAST and BLAST 2.0 algorithms, which are separately described in Altschul et al. (1977) Nucl. Acid. Res. 25: 3389-3402 and Altschul et al. (1990) J. Mol. Biol. 215: 403-410. The BLAST and BLAST 2.0 can be used to determine the identity percentages of the amino acid sequences of the invention by using, for example, parameters as described in the literatures or default parameters. The software that performs BLAST analysis can be obtained through the National Biotechnology Information Center.

In the present invention, those amino acid sequences having at least 70% sequence identity to the amino acid sequence comprises polypeptide sequences substantially identical to the amino acid sequence, for example, when the method described herein (e.g., BLAST analysis using standard parameters) is used, those amino acid sequences with at least 70% sequence identity in comparison with the polypeptide sequence of the present invention, preferably at least 75%, 80%, 85%, 86%, 87%, 88%, 89%, 90%, 91%, 92%, 93%, 94%, 95%, 96%, 97%, 98%, 99% or greater sequence identity to the polypeptide sequences of the present invention.

In the present invention, the toxins used for the antibody-drug conjugate include diphtheria toxin A chain, non-binding active fragments of diphtheria toxin, exotoxin A chain (from *Pseudomonas aeruginosa*), ricin A chain, abrin A chain, modeccin A chain, α-sarcin, Aleutites fordii toxic protein, dianthin toxic protein, Phytolacaamericana toxic proteins (PAPI, PAPII and PAP-S), *Momordica charantia* inhibitors, curcin, crotin, *Sapaonaria officinalis* inhibitors, gelonin, mitogellin, restrictocin, phenomycin, enomycin, and trichothecenes. See also: e.g., WO 93/21232 published on Oct. 28, 1993.

A variety of radionuclides can be used to generate the antibody-drug conjugates. Examples include $^{212}$Bi, $^{131}$I, $^{131}$In, $^{90}$Y, and $^{186}$Re.

The antibody-cytotoxic agent conjugates can be prepared using a variety of bifunctional protein coupling agents, such as bifunctional derivatives, for example, N-succinimidyl 3-(2-pyridyldithio)propionate (SPDP), iminothiolane (IT), imidates (e.g., dimethyl adipimidate dihydrochloride), active esters (e.g., disuccinimidyl suberate), aldehydes (e.g., glutaraldehyde), bisazide compounds (e.g., bis(p-diazido-benzoyl)hexamethylenediamine), bisdiazo compounds (e.g., bis(p-diazobenzoyl)-ethylenediamine), diisothiocyanates (e.g., toluene-2,6-diisocyanate), and double active fluorine compounds (e.g., 1,5-difluoro-2,4-dinitrobenzene). For example, it can be a ricin-containing immunotoxin prepared as described by Vitetta et al. (1987) Science, 238: 1098. The carbon-14 labeled 1-isothiocyanic acid benzyl-3-methyldiethylenetriamine pentaacetic acid (MX-DTPA) is an exemplary chelating agent for coupling radioactive nucleotides with antibodies (WO94/11026). The invention also comprises a conjugate of an antibody and one or more small molecule toxins (e.g., calicheamicin, maytansinoid, dolastatin, auristatin, trichothecene, and CC 1065, as well as toxic derivatives of these toxins).

In some embodiments, the antibody-drug conjugate comprises an anti-epidermal growth factor receptor antibody coupled to dolastatin or a dolastatin peptide analogue and derivative auristatin (U.S. Pat. Nos. 5,635,483; 5,780,588). Dolastatin and auristatin have shown activities of interfering with microtubule kinetics, GTP hydrolysis, and nuclear and cell division (Woyke et al. (2001) Antimicrob. Agents and Chemother. 45 (12): 3580-3584), and have anticancer activity (U.S. Pat. No. 5,663,149) and antifungal activity (Pettit et al. (1998) Antimicrob. Agents Chemother. 42: 2961-2965). The drug modules of dolastatin or auristatin can be attached to an antibody via N (amino) terminus or C (carboxy) terminus of the peptide drug modules (WO 02/088172).

In the present invention, the structure of MMAE is:

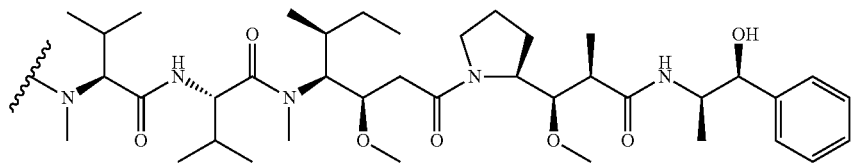 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@H](C)[C@@H](O)c1ccccc1)OC)C(C)C)C(C)C]

In the present invention, the structure of MMAF is:

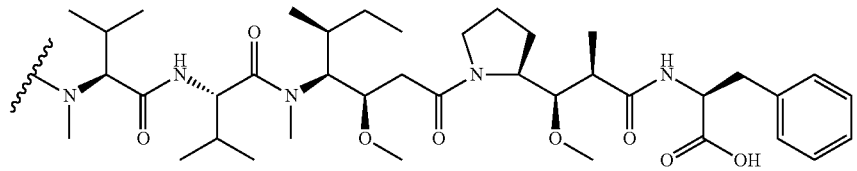 [SMILES: *N(C)[C@H](C(=O)N[C@H](C(=O)N(C)[C@@H]([C@@H](C)CC)[C@@H](CC(=O)N1CCC[C@H]1[C@H](OC)[C@@H](C)C(=O)N[C@@H](Cc1ccccc1)C(=O)O)OC)C(C)C)C(C)C]

In the present invention, an enzyme as cytotoxic agent may be a compound having nucleic acid degradation activity (e.g., ribonuclease or DNA endonuclease, such as deoxyribonuclease; DNA enzyme).

In the present invention, the drug load is represented by p, i.e., the average number of drug modules (i.e., cytotoxic agents) of each antibody in the molecule of formula I:

Ab-(L-D)$_p$. The drug load can range from 1 to 20 drug modules (D) per antibody. The ADC of Formula I includes a collection of antibodies conjugated to a range of (1-20) drug modules. The average number of drug modules per antibody from the ADC preparation of coupling reaction can be verified by conventional means, such as mass spectrometry, ELISA assay, and HPLC. The quantitative distribution of ADCs in respect of p can also be determined. In some cases, homogeneous ADCs with p of certain value can be isolated from ADCs with other drug loadings, and purification and validation can be achieved by means such as reverse phase HPLC or electrophoresis.

For some antibody-drug conjugates, p may be limited by the number of attachment sites on the antibody. For example, if the attachment site is a cysteine thiol, the antibody may have only one or several cysteine thiol groups, or may have only one or more thiol groups with sufficient reactivity to attach the linkers. In certain embodiments, a higher drug load, such as p>5, may cause aggregation, insolubility, toxicity, or loss of cell permeability of certain antibody-drug conjugates.

In certain embodiments, the ADCs of the invention have a drug load ranging from 1 to about 8; from about 2 to about 6; from about 3 to about 5; from about 4 to about 5; from about 3.5 to about 4.5; about 4. In fact, it has been shown that some ADCs had an optimal drug load of less than 8, or from about 2 to about 5, for each antibody. See US2005-0238649A1 (which is fully incorporated herein by reference).

In certain embodiments, drug modules less than the theoretical maximum are conjugated to the antibody in the coupling reaction. The antibody may comprise, for example, a lysine residue that does not react with a drug-linker intermediate or a linker reagent. In general, the antibody does not contain a number of free and reactive cysteine thiol groups, which can be linked to a drug moiety; in fact, most of the cysteine thiol groups in the antibody are present in the form of a disulfide bridge. In certain embodiments, the antibody may be reduced with a reducing agent such as dithiothreitol (DTT) or tricarbonyl ethyl phosphine (TCEP) under partial or complete reductive conditions to produce a reactive cysteine thiol group. In certain embodiments, the antibody is placed under denaturing conditions to expose a reactive nucleophilic group, such as lysine or cysteine.

The loading (drug/antibody ratio) of ADC may be controlled in different ways, for example, by: (i) limiting the mole number of drug-linker or linker reagent relative to the antibody, (ii) limiting the time or temperature of the coupling reaction, (iii) modifying cysteine thiol moieties or restricting reduction conditions, (iv) performing engineering reconstruction of amino acid sequences of the antibodies by recombinant techniques, such that the number and location of cysteine residues are changed in order to control the number and/or location of the linker-drug attachments. It is to be understood that if more than one nucleophilic group is reacted with a drug-linker intermediate or with a linker reagent and a subsequent drug module reagent, the resulting product is an ADC compound mixture having one or more drug modules attached to the antibody. The average number of drug modules per antibody can be calculated from the mixture by an antibody-specific and drug-specific double-ELISA antibody assay. The various ADC molecules in the mixture can be identified by mass spectrometry and separated by HPLC, for example, hydrophobic interaction chromatography. In certain embodiments, a homogeneous ADC with a single loading value can be isolated from the coupling mixture by electrophoresis or chromatography.

In the present invention, the pharmaceutically acceptable salts of the antibody-drug conjugates include acid addition salts of inorganic acids, carboxylic acids and sulfonic acids, for example, salts of the following acids: hydrochloric acid, hydrobromic acid, sulfuric acid, phosphoric acid, methanesulfonic acid, ethanesulfonic acid, benzenesulfonic acid, toluenesulfonic acid, naphthalene disulfonic acid, acetic acid, trifluoroacetic acid, propionic acid, lactic acid, tartaric acid, malic acid, citric acid, fumaric acid, maleic acid and benzoic acid.

The pharmaceutically acceptable salts of the antibody-drug conjugates of the present invention also include salts of conventional bases, for example (merely exemplified and preferred), alkali metal salts (e.g., sodium salts and potassium salts), alkaline earth metal salts (e.g., calcium salts and magnesium salts) and ammonium salts derived from ammonia or organic amines containing from 1 to 16 carbon atoms, in which the organic amines are, for example (merely exemplified and preferred), ethylamine, diethylamine, triethylamine, ethyl diisopropylamine, monoethanolamine, diethanolamine, triethanolamine, dicyclohexylamine, dimethylaminoethanol, procaine, dibenzamide, N-methylpiperidine, N-methylmorpholine, arginine, lysine and 1,2-ethylenediamine.

In the present invention, the solvate represents these forms of the antibody-drug conjugate of the present invention: complexes in solid or liquid form that are formed by coordination of the antibody-drug conjugate with solvent molecules. Hydrate is a specific form of the solvate which has coordinating water molecules. In the present invention, the hydrate is the preferred solvate.

The EGFR-associated tumors that can be preferably treated with the antibody-drug conjugates of the invention include tumors with EGFR overexpression, respiratory tract tumors (e.g., small cell carcinoma and non-small cell carcinoma, bronchial carcinoma), wherein non-small cell lung cancer is particularly preferred; tumors of digestive tracts (e.g., esophagus, stomach, gallbladder, small intestine, large intestine, rectum), wherein intestinal tumor is particularly preferred; tumors of endocrine and exocrine glands (e.g., thyroid and parathyroid, pancreas and salivary glands), wherein pancreatic tumor is particularly preferred; tumors of head and neck regions (e.g., larynx, hypopharynx, nasopharynx, oropharynx, lips, mouth, tongue and esophagus); and/or gliomas.

In the present invention, EGFR overexpression means that the expression level of EGFR is increased as compared with the level of EGFR expression on the surface of normal epithelial cells; specifically, it can be divided into high expression, moderate expression and low expression, for example, DiFi cells are EGFR high expression cell lines, LoVo cells are EGFR moderate expression cell lines, while HT-29 cells are EGFR low expression cell lines (Wild, R., et al., Mol. Cancer Rher 2006: 5 (1), p 104-113, Cetuximab preclinical antitumor activity (monotherapy and combination based) is not predicted by relative total or activated epidermal growth factor receptor tumor expression levels).

The antibody-drug conjugates of the present invention may be used in combination with a known chemotherapeutic agent for the treatment of tumors, the chemotherapeutic agent can be, for example, Adriamycin, cyclophosphamide and taxane [Taxol and Taxotere], Xeloda, Gemzar, Navelbine, Tamoxifen, aromatase inhibitors (Arimidex, Femara, Aromasin), 5-FU plus folinic acid, camptosar, oxaliplatin, cisplatin, carboplatin, estramustine, Novantrone, prednisone, Oncovin, etc., or a combination thereof.

In the present invention, "treatment" refers to clinical intervention that attempts to alter the natural course of a treated individual or cell, either for prevention or in the course of clinical pathology. The desired effect of treatment includes the prevention of recurrence or relapse of disease, the alleviation of symptoms, the weakening of any direct or indirect pathological consequences of disease, the prevention of metastasis, the reduction of disease progression rate, the improvement or alleviation of disease status, and the elimination or improvement of prognosis. In some embodiments, the antibody or antibody-drug conjugate of the invention is used to delay the onset of a disease or condition or to slow down the progression of a disease or condition. The above parameters used to assess the successful treatment and improvement of disease can be easily measured by conventional procedures familiar to physicians. For cancer treatment, efficacy can be measured by, for example, assessing time to progress (TTP) and/or measuring response rate (RR).

In the present invention, "subject" refers to a vertebrate. In certain embodiments, the vertebrate refers to a mammal. The mammal includes, but is not limited to, livestock (such as cattle), pets (such as cats, dogs, and horses), primates, mice and rats. In certain embodiments, the mammal refers to a human.

In the present invention, "effective amount" refers to an amount effective to achieve the desired therapeutic or prophylactic effect at the desired dose and time. The "therapeutically effective amount" of a substance/molecule of the invention may vary depending on factors such as disease state, age, gender and body weight of an individual and the ability of the substance/molecule to elicit a desired response in the individual. The therapeutically effective amount also covers an amount of the substance/molecule of which beneficial effects are superior to any toxic or detrimental effect. "Prophylactically effective amount" refers to an amount effective to achieve the desired prophylactic effect at the desired dose and time. It is generally but not necessary, however, that the prophylactically effective amount will be lower than the therapeutically effective amount since the prophylactic dose is administered to the subject prior to the onset of the disease or early in the disease. In the case of cancer, the therapeutically effective amount of the drug can reduce the number of cancer cells; reduce the tumor volume; inhibit (i.e., slow down to some extent, preferably stop) the cancer cells infiltrating into the surrounding organs; inhibit (i.e., slow down to some extent, preferably stop) tumor metastasis; inhibit to some extent the growth of tumor; and/or alleviate to some extent one or more symptoms associated with cancer.

For the prophylaxis or treatment of the disease, the appropriate dosage of the antibody-drug conjugate of the invention (when used alone or in combination with one or more other therapeutic agents such as chemotherapeutic agents) will depend on the type of disease to be treated, the type of the antibody-drug conjugate, the severity and progression of the disease, the administration of the antibody-drug conjugate that is for the purpose of prevention or treatment, the previous therapy, the patient's clinical history and reactivity with the antibody-drug conjugates, judgment of physicians. Suitably, the antibody-drug conjugate is administered to the patient either once or through a series of treatments. Depending on the type and severity of the disease, the initial candidate dose administered to the patient may be about 1 µg/kg to 100 mg/kg (e.g., 0.1 mg/kg to 20 mg/kg) of the antibody-drug conjugate, for example or by one or more separate administrations or by continuous infusion. Depending on the factors described above, the typical daily dose may range from about 1 µg/kg to 100 mg/kg or more. For repeated administrations for several days or more, depending on the conditions, the treatment is usually continued until the desired inhibition of symptoms appears. An exemplary dose of the antibody-drug conjugate may range from about 0.05 mg/kg to about 10 mg/kg. As such, the antibody-drug conjugate of one or more doses of about 0.5 mg/kg, 2.0 mg/kg, 4.0 mg/kg or 10 mg/kg (or any combination thereof) may be administered to the patient. Such doses may be administered intermittently, for example, weekly or every three weeks (e.g., such that the patient receives about 2 to about 20 doses, or, for example, about 6 doses of the antibody-drug conjugate). A higher initial loading dose may be administered, followed by one or more doses of lower dose. The process of this therapy is easily monitored by conventional techniques and assays. "Long term" administration refers to the fact that the initial therapeutic effect (activity) is maintained for a longer period of time, in contrast to the short-term pattern, in a continuous mode of administration of the agent. "Intermittent" administration refers to treatment that is not continuous without interruption, but is essentially periodic. Administration in "combination" with one or more other therapeutic agents includes simultaneous (co-) administration and sequential administration in any order.

"Pharmaceutically acceptable carriers" include, when used in the present invention, pharmaceutically acceptable carriers, excipients or stabilizers, which are non-toxic to the cells or mammals to which they are exposed at the dosage and concentration employed. Typically, a physiologically acceptable carrier is a pH buffered aqueous solution. Examples of physiologically acceptable carriers include buffers such as phosphates, citrates and other organic acids; antioxidants including ascorbic acid; low molecular weight (less than about 10 residues) polypeptides; proteins such as serum albumin, gelatin or immunoglobulins; hydrophilic polymers such as polyvinylpyrrolidone; amino acids such as glycine, glutamine, asparagine, arginine or lysine; monosaccharides, disaccharides and other carbohydrates, including glucose, mannose, sucrose, trehalose or dextrin; chelating agents such as EDTA; sugar alcohols such as mannitol or sorbitol; salt-forming counterions such as sodium; and/or nonionic surfactants such as TWEEN™, polyethylene glycol (PEG) and PLURONICS™.

In the present invention, the KRAS gene has the same meaning as the K-RAS gene, which is a member of RAS gene family and encodes K-ras protein, which is related to the generation, proliferation, migration, diffusion and angiogenesis of various tumors. Its common mutation sites are codon 12 and codon 13 of exon 2 of K-RAS gene, and codon 61 of exon 3, among which there are 7 mutation hot spots: G12C, G12R, G12S, G12V, G12D, G12A, G13V/D. These seven mutations account for more than 90%. In one embodiment of the invention, the tumor is a tumor with KRAS gene mutation that is associated with EGFR overexpression.

In the present invention, BRAF (v-raf murine sarcoma viral oncogene homolog B1) gene is a proto-oncogene and is a member of the RAF family. Approximately 8% of human tumors have BRAF mutations, and most of the BRAF gene mutations are BRAFV600E mutations that lead to the continued activation of downstream MEK/ERK signaling pathways, which are critical for tumor growth and invasion and metastasis. In one embodiment of the invention, the tumor is a tumor with BRAF gene mutation that is associated with EGFR overexpression.

In the present invention, 20 conventional amino acids and their abbreviations follow their conventional usages. See

SPECIFIC MODELS FOR CARRYING OUT THE INVENTION

Figure 1:
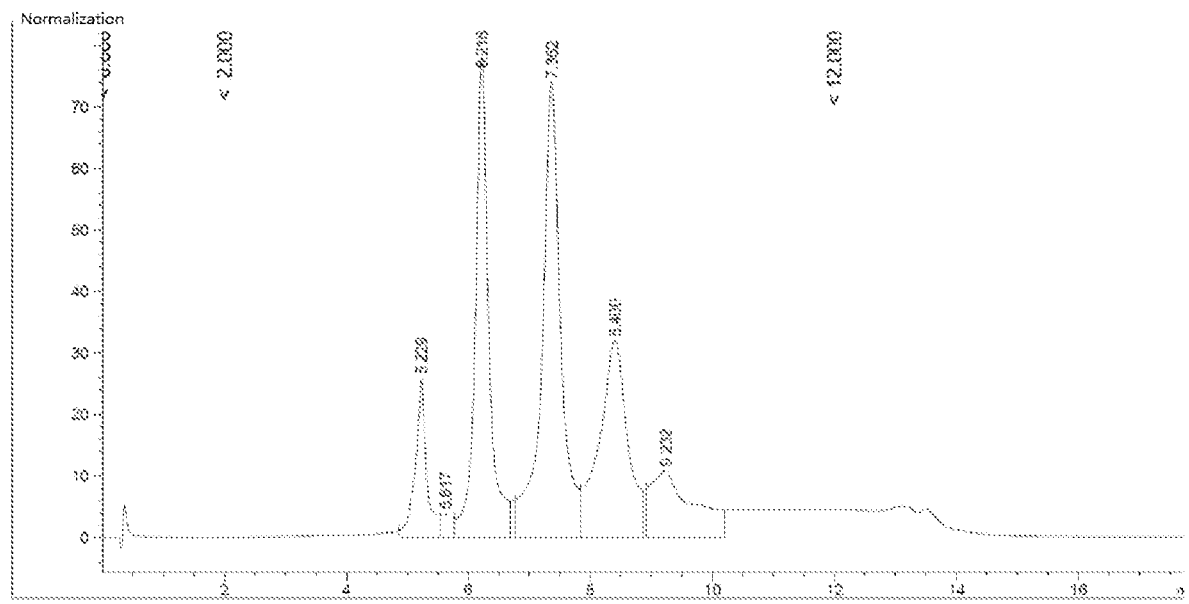
FIG. 1 shows a HIC-HPLC plot for determining the drug/antibody ratio of antibody-drug conjugates.

The embodiments of the present invention will be described in details with reference to the following examples, and it will be understood by those skilled in the art that the following examples are intended to be illustrative of the invention and are not to be taken as limiting the scope of the invention. When specific conditions in the examples were not given, they were carried out in accordance with conventional conditions or the conditions recommended by the manufacturers. When reagents or instruments as used were not indicated with the manufacturers, they were conventional products commercially available in the market.

The antibody BA03 of the present invention was BA03 as described in the Chinese invention patent application CN 103772504A, and its preparation method could be seen in Example 3 of this patent application. The sequences of every part of the antibody were as follows:

The sequence of the variable region of heavy chain was:

(SEQ ID NO: 1)
QVQLQESGPGLVKPSETLSLTCTVSGFSLS<u>NYDVH</u>WVRQAPGKGLEWLG<u>V</u>

<u>IWSGGNTDYNTPFTS</u>RLTISVDTSKNQFSLKLSSVTAADTAVYYCAR<u>ALD</u>

<u>YYDYEFAY</u>WGQGTLVTVSS.

wherein the underlined parts were CDR1 (SEQ ID NO: 5), CDR2 (SEQ ID NO: 6), CDR3 (SEQ ID NO: 7), respectively;

the non-underlined parts were FR1 (SEQ ID NO: 8), FR2 (SEQ ID NO: 9), FR3 (SEQ ID NO: 10), FR4 (SEQ ID NO: 11), respectively.

The sequence of the variable region of light chain was:

(SEQ ID NO: 2)
EIVLTQSPDFQSVTPKEKVTITC<u>RASQSIGTNIH</u>WYQQKPDQSPKLLIK<u>Y</u>

<u>ASESISG</u>IPSRFSGSGSGTDFTLTINSLEAEDAATYYC<u>QQNNEWPTSF</u>GQ

GTKLEIK.

wherein the underlined parts were CDR1 (SEQ ID NO: 12), CDR2 (SEQ ID NO: 13), CDR3 (SEQ ID NO: 14), respectively;

the non-underlined parts were FR1 (SEQ ID NO: 15), FR2 (SEQ ID NO: 16), FR3 (SEQ ID NO: 17), FR4 (SEQ ID NO: 18), respectively.

The sequence of constant region of heavy chain was:

(SEQ ID NO: 3)
ASTKGPSVFPLAPSSKSTSGGTAALGCLVKDYFPEPVTVSWNSGALTSGV

HTFPAVLQSSGLYSLSSVVTVPSSSLGTQTYICNVNHKPSNTKVDKRVEP

KSCDKTHTCPPCPAPELLGGPSVFLFPPKPKDTLMISRTPEVTCVVVDVS

HEDPEVKFNWYVDGVEVHNAKTKPREEQYNSTYRVVSVLTVLHQDWLNGK

EYKCKVSNKALPAPIEKTISKAKGQPREPQVYTLPPSREEMTKNQVSLTC

LVKGFYPSDIAVEWESNGQPENNYKTTPPVLDSDGSFFLYSKLTVDKSRW

QQGNVFSCSVMHEALHNHYTQKSLSLSPGK.

The sequence of constant region of light chain was:

(SEQ ID NO: 4)
RTVAAPSVFIFPPSDEQLKSGTASVVCLLNNFYPREAKVQWKVDNALQSG

NSQESVTEQDSKDSTYSLSSTLTLSKADYEKHKVYACEVTHQGLSSPVTK

SFNRGEC.

Example 1: Preparation of Antibody-Drug Conjugate 10 mg of BA03 antibody was buffer exchanged using a 15 mL 30 KD ultrafiltration device into a reduction buffer (25 mM sodium borate, pH 8.0, 25 mM NaCl, 5 mM EDTA) for a total of three times; the final volume was about 1 mL, transferred to a new Eppendorf centrifuge tube (weighed), and weighed; the protein concentration was measured and the total amount of protein was calculated. 2.5 times molar amount of DTT was added to the antibody and incubated at room temperature for 2 hours and continuously mixed. The mixture was buffer exchanged using a 15 ml 30 KD ultrafiltration device into a coupling buffer (50 mM Tris, pH 7.2, 150 mM NaCl, 5 mM EDTA) for a total of three times. The concentrated solution was taken and weighed, measured by A280 to determine protein concentration, and the total amount of protein was calculated. 10 μl sample was taken and measured by Ellman's method to determine number of free thiol groups.

In addition, the molar concentration of its free thiol groups was calculated by the following formula:

$$C_{thiol} = \frac{A412 \times 112}{b \times 14150}(M)$$

b: optical path length of cuvette (usually 1 cm).

The mole number of free thiol groups was calculated from the molar concentration of free thiol groups and the volume of total protein solution.

To the reduced antibody was added 1.1 times the mole number of free thiol groups of vc-MMAE (purchased from Haoyuan Chemical Technology Co., Ltd., No. HY-15575) (dissolved in DMSO), mixed at room temperature and reacted for 2 hours, intermittently mixed. To the reaction system was added with N-acetylcysteine in an amount of 20 times the mole number of vc-MMAE in the reaction solution, mixed, and the mixture was allowed to stand for 5 minutes. The mixture was buffer exchanged using a 15 ml 30 KD ultrafiltration device into a conjugate stock solution (20 mM sodium citrate (Na-citrate), 0.3% NaCl, 5% Trehalose, 0.05% TWeen-80, pH 6.0) for a total of 3 times. The obtained antibody-drug conjugate MYK-3 sample was stored at 4° C.

Determination of Drug/Antibody Ratio:

The prepared antibody-drug conjugate MYK-3 was analyzed by HIC-HPLC analysis (Jun Ouyang, Drug-To-Antibody (DAR) Ratio and Drug Distribution by Hydrophobic Interaction Chromatography and Reverse Phase High Performance Chromatography, Laurent Ducry (ed.), Antibody Drug Conjugates, Chapter 17, Methods in Molecular Biology, Vol 1045, p 275-283) to determine the drug/antibody ratio (DAR), the results were shown in FIG. 1, and the average drug load DAR was calculated as 4.1 according to the peak area.

Example 2: Detection of Inhibition Activity of Antibody-Drug Conjugate MYK-3 on Cells in Vitro Method for Detection of Inhibition Activity on Cells:

1.1 After 3-4 times of passages of the thawed cell lines, the culture media were firstly discarded, the cells were rinsed with 5 mL of DPBS once, and then digested with 3 mL of trypsin, resuspended respectively with media, centrifuged with a centrifuge, and the supernatants were discarded. And then the cells were resuspended again with the media, and 0.5 mL samples were taken and counted with a cell counter. The cells were plated on 96-well cell plates (DiFi cells at 10,000 cells/well, HT-29 cells at 5000 cells/well, A549 cells at 2000 cells/well, U87-MG cells at 3000 cells/well, LoVo cells at 4000 cells/well), cultured for 24 hours, then monoclonal antibody BA03 and antibody-drug conjugate MYK-3 as diluted in a series of concentrations were added and incubated in a cell culture incubator for 72 hours. Each well was then added with 20 μl of CCK8 color-producing reagent, measured at wave length of 450-650 nm with a microplate reader to determine OD450-650 values, and fitted with four parameters logistic model.

Results of the Detection of Inhibition Activity on Cells In Vitro:

The following cell lines were purchased from Shanghai Institute of Cell Biology, Chinese Academy of Sciences.

Figure 2:
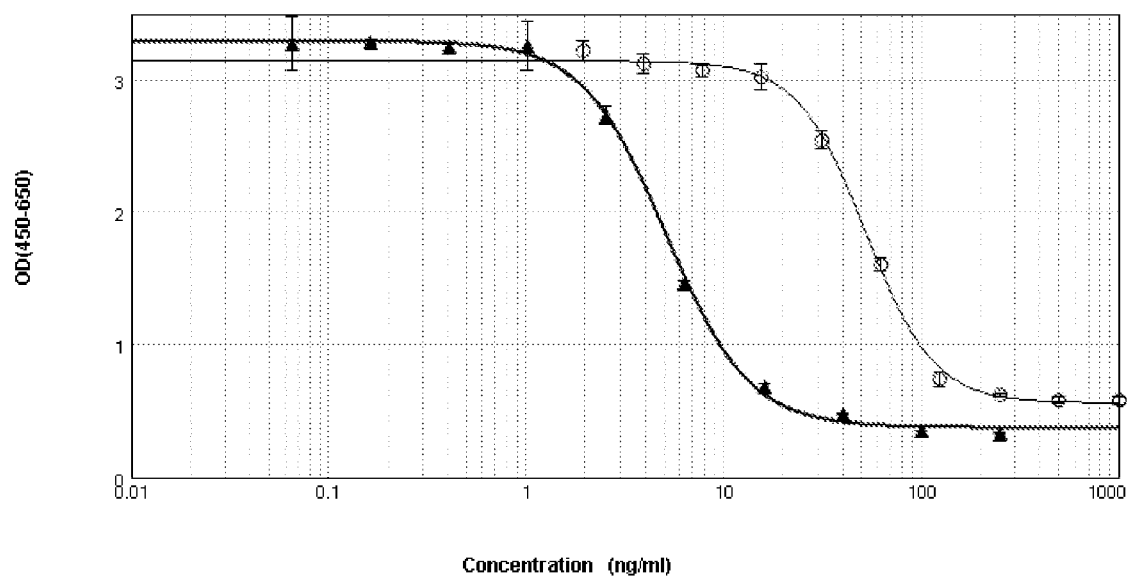
FIG. 2 shows results of detection of inhibition activity on cells in vitro of monoclonal antibody and antibody-drug conjugate, wherein ○ represents BA03 monoclonal antibody, ▲ represents MYK-3 antibody-drug conjugate.

Regarding the activities in EGFR-overexpressing DiFi cells (human colorectal cancer cells): MYK-3 showed a significantly increased cell growth inhibitory activity than monoclonal antibody BA03, while EC50 decreased by about 10-fold (EC50 of BA03 was 51.9 ng/ml, EC50 of MYK-3 was 5.1 ng/ml), as shown in FIG. 2.

Figure 3:
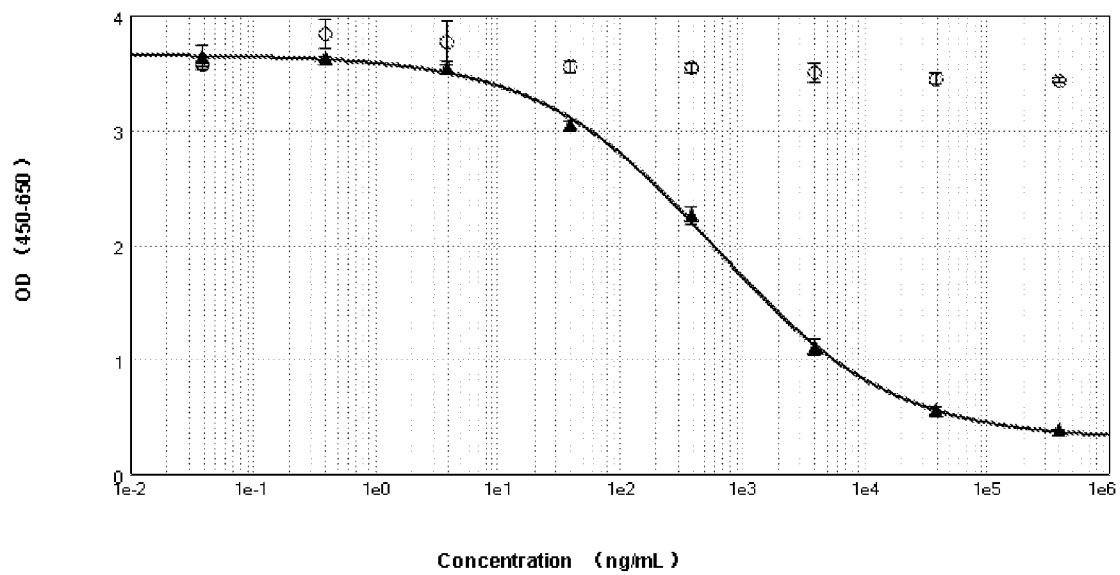
FIG. 3 shows inhibition activity of MYK-3 on the growth of colon cancer cell line HT-29, wherein ○ represents BA03 monoclonal antibody and ▲ represents MYK-3 antibody-drug conjugate.
Figure 4:
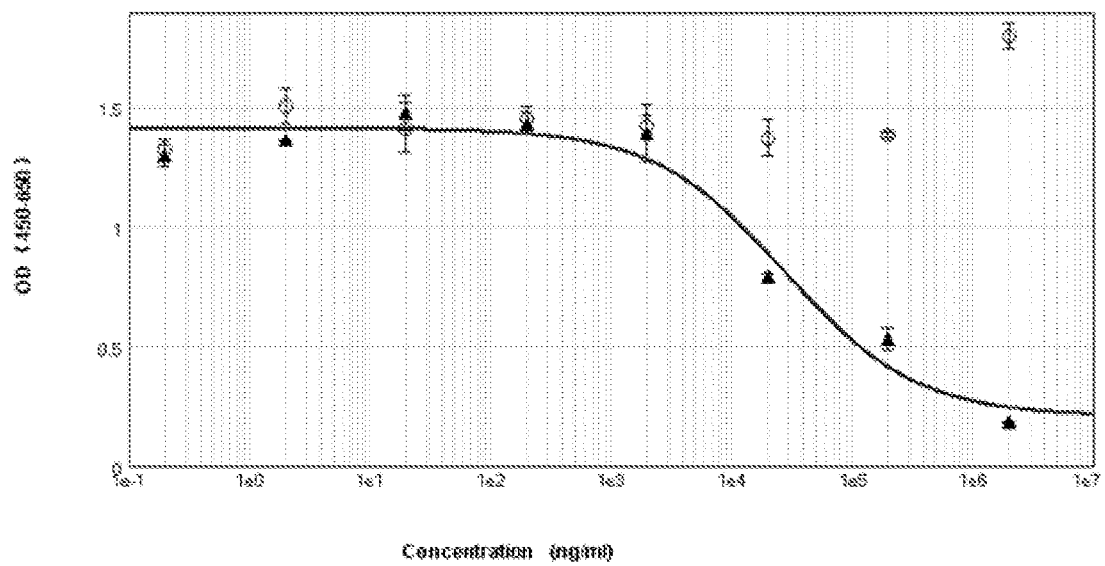
FIG. 4 shows inhibition activity of MYK-3 on the growth of glioma cell U87-MG, where ○ represents BA03 monoclonal antibody and ▲ represents MYK-3 antibody drug conjugates.
Figure 5:
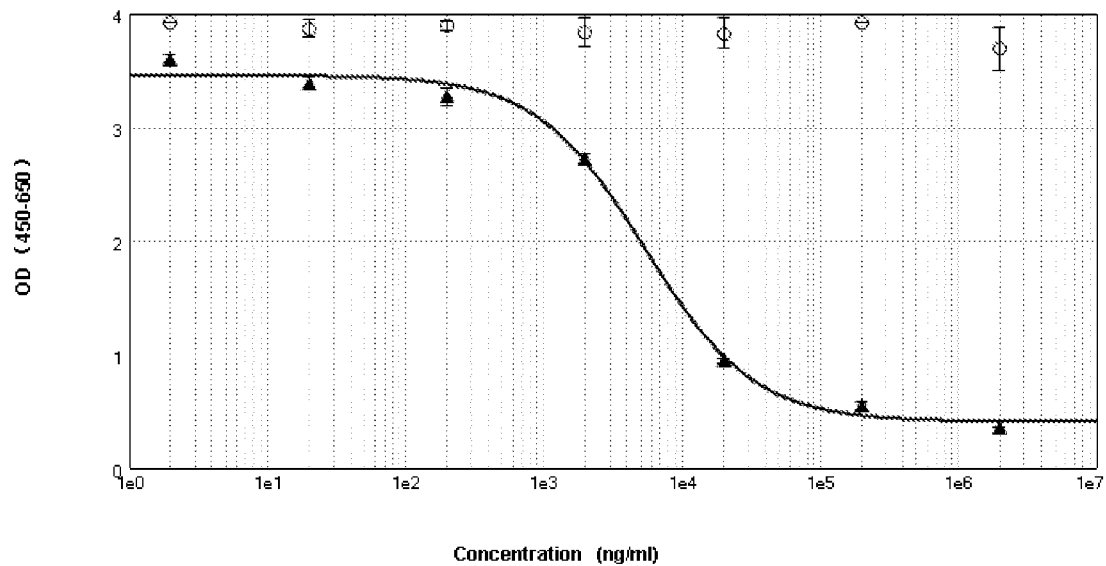
FIG. 5 shows inhibition activity of MYK-3 on the growth of lung cancer cell A549, wherein ○ represents BA03 monoclonal antibody, and ▲ represents MYK-3 antibody-drug conjugate.

Regarding the activities in other tumor cells with moderate expression and low expression of EGFR: MYK-3 showed significant cell growth inhibitory activity relative to monoclonal antibody itself in cancer cells (human colon cancer cells HT29, human lung cancer cell A549, human brain astrocytoma cell line U87-MG) with moderate expression and low expression of EGFR (as shown in FIG. 3, FIG. 4, FIG. 5), wherein EC50 of HT-29 was 611 ng/ml, EC50 of A549 was 28.3 μg/ml, and EC50 of U87-MG was 5.3 μg/ml.

Figure 6:
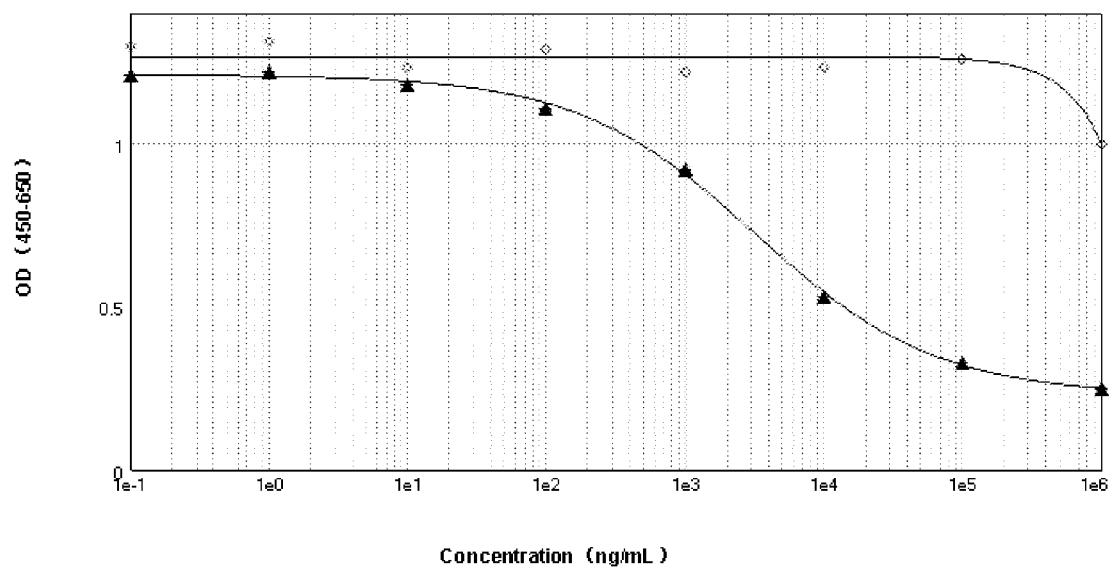
FIG. 6 shows inhibition activity of MYK-3 on the growth of KRAS mutant colon cancer cell LoVo, in which ◇ represents levofloxacin monoclonal antibody and ▲ represents MYK-3 antibody-drug conjugate.

In addition, we also tested activities in KRAS mutant colon cancer cells LoVo (Dunn E F, Ilda M, Myers R A, Hintz K A, Campbell D A, Armstrong E A, Li C and Wheeler D L. Dasatinib sensitizes KRAS mutant colorectal tumors to cetruximab. Oncogene 2011; 30: 561-574) with moderate EGFR expression, and found that MYK-3 showed significant tumor growth inhibitory activity to KRAS mutant colon cancer cell LoVo (as shown in FIG. 6, EC50 was 3.2 μg/ml), whereas BA03 alone had little inhibitory activity to the cell line.

Example 3: In Vivo Tumor Xenograft Test in Mice

Experimental Method of In Vivo Tumor Xenograft Test in Mice:

HT-29 colon cancer cells were cell lines with relatively low expression of EGFR and with BRAF mutations, and the EGFR targeting monoclonal antibody Erbitux as currently marketed for the treatment of colorectal cancer had no growth inhibitory activity to HT-29 cell strains.

HT-29 cell xenograft model: the tumor cells at logarithmic growth phase were collected and counted, then resuspended in 1×PBS. The cell suspension concentration was adjusted to $3 \times 10^7$/ml. The tumor cells were inoculated subcutaneously on the right side of back of nude mice with a 1 ml syringe (4 gauge needle), $3 \times 10^6$/0.1 ml/mouse. When the tumor volume reached 150-200 mm$^3$, the mice were grouped by a randomized block method, 8 mice per group, so as to ensure that the tumor volume and body weight of mice between the groups were uniform. The difference between the mean value of tumor volume in each group and the mean value of tumor volume of all experimental animals was not more than ±10%. Tail vein administration was performed, once every four days (the 1$^{st}$, 5$^{th}$, 9$^{th}$ and 13$^{th}$ day), for a total of 4 times, and the tumor volumes and body weights of mice were regularly measured. There were 8 mice in each administration group.

Experimental Results of Tumor Xenograft Study in Mice

Figure 7:
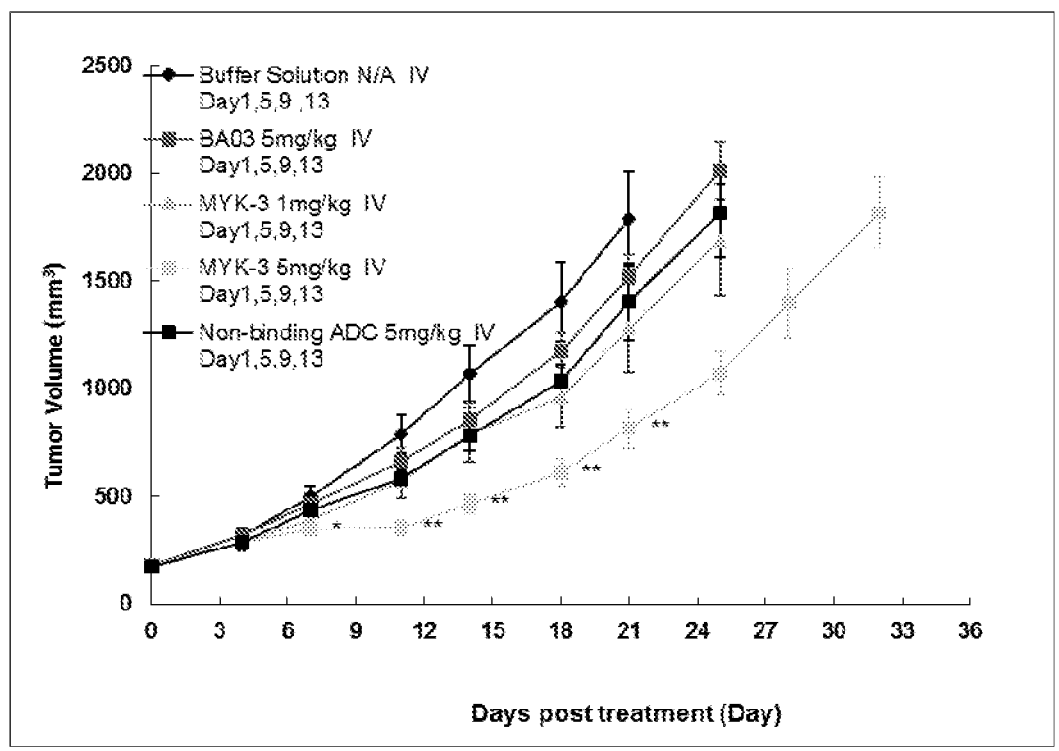
FIG. 7 shows effects of monoclonal antibody and antibody-drug conjugates on volume of HT-29 colon cancer xenografted tumor in mice, in which the data are expressed as the mean±standard deviation; * indicates P<0.05,  indicates P<0.01, and * indicates P<0.001, as compared with the buffer control group.

HT-29 colon cancer xenograft test in mice: there were 5 groups in the test, including buffer solution group as vehicle control (20 mM sodium citrate, 0.3% sodium chloride, 5% trehalose, 0.05% Tween 80, pH 6), BA03 monoclonal antibody group (5 mg/kg), MYK-3 group (1 mg/kg), MYK-3 group (5 mg/kg) and non-binding ADC group (5 mg/kg) (human IgG-vcMMAE conjugate, in which IgG was IgG obtained by purification from human serum, and this conjugate was prepared by the same method as MYK-3). The tumor volume in the mice administrated with MYK-3 was significantly lower than that of the control group, showing a significant anti-tumor growth effect (FIG. 7). On the 18$^{th}$ day, for the group of MYK-3 at dose of 5 mg/Kg, its tumor growth inhibition rate was up to 54% as compared with the buffer group, and its tumor growth inhibition rate was up to 46% as compared with the group of monoclonal antibody BA03 at the same dose, and its tumor growth inhibition rate was up to 42% as compared with the non-binding ADC.

Figure 8:
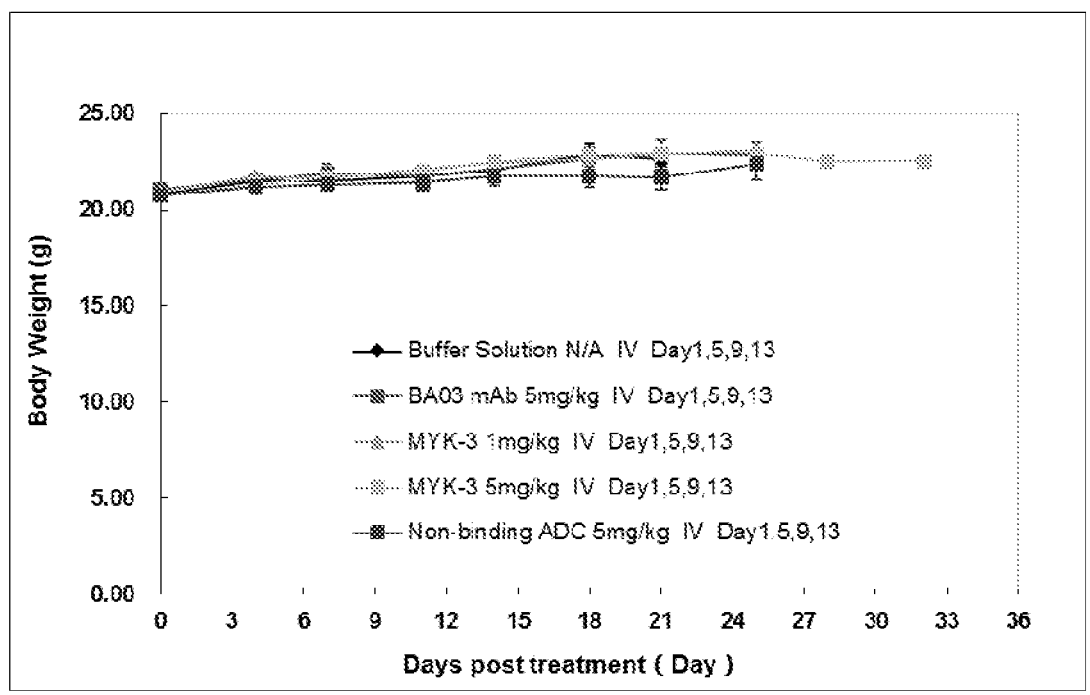
FIG. 8 shows effects of monoclonal antibody and antibody-drug conjugate on body weight of mice of HT-29 colon cancer xenograft model.

Body weight of mice: the body weight of mice administrated with MYK-3 showed no significant change as compared with the control group (see FIG. 8), indicating that MYK-3 had not toxic effect of reducing body weight of mice.

Figure 9:
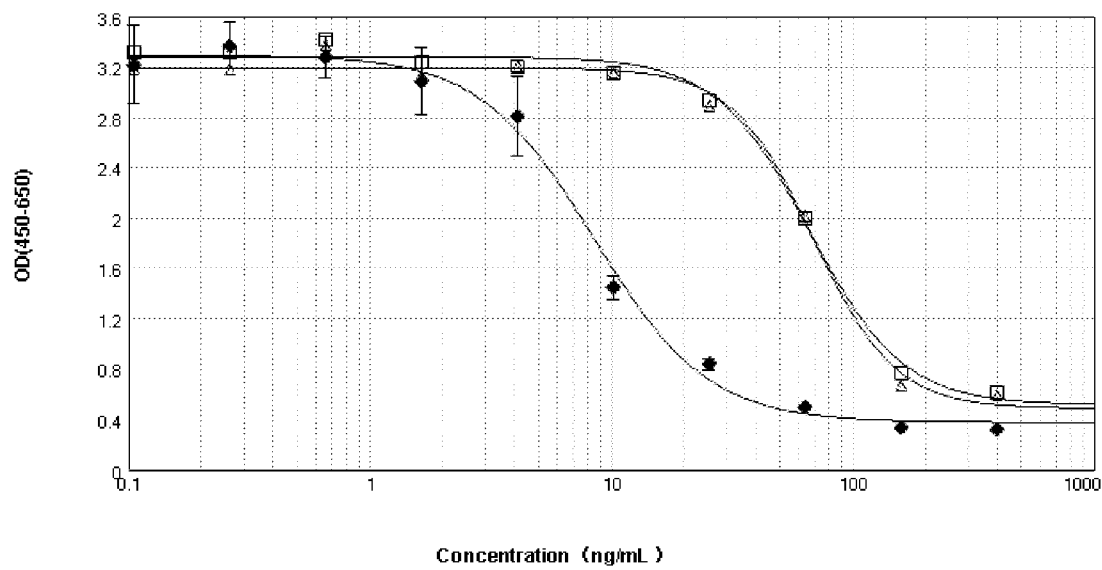
FIG. 9 shows inhibition activity of MYK-3, monoclonal antibody BA03 and BA03+ equimolar vcMMAE on the growth of colorectal cancer cell DiFi, wherein □ represents monoclonal antibody component BA03 of MYK-3, ▲ represents monoclonal antibody BA03 plus vcMMAE in an amount equivalent to MYK-3 drug-loading moles, ♦ represents MYK-3.

Example 4: Inhibitory Activities of MYK-3, Monoclonal Antibody BA03 and BA03+ Equimolar vcMMAE on Growth of Colorectal Cancer Cell DiFi The inhibitory activities of MYK-3, monoclonal antibody BA03 and BA03+equimolar vcMMAE on the growth of colorectal cancer cell DiFi were determined according to the method of Example 2, and the experimental results were shown in FIG. 9, in which EC50 values were 8.4 ng/mL, 65.8 ng/ML and 68.2 ng/mL, respectively.

Figure 10:
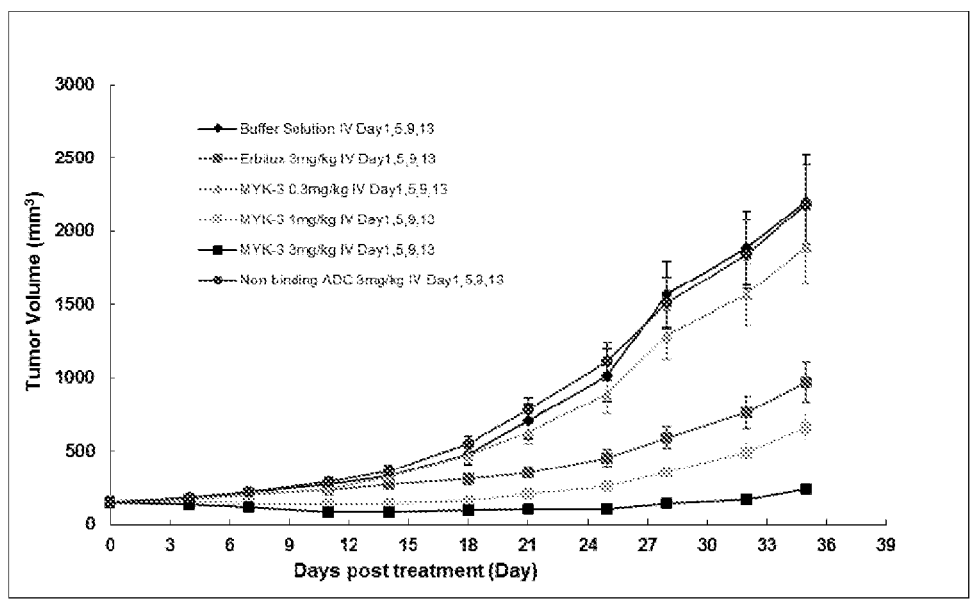
FIG. 10 shows inhibition activity of MYK-3 on the growth of KRAS mutant colon cancer cell LoVo in nude mice.

Example 5: Inhibitory Activity of MYK-3 on the Growth of Transplanted Tumor of KRAS Mutant Colon Cancer Cell LoVo in Nude Mice The inhibitory activity of MYK-3 on the growth of transplanted tumor of KRAS mutant colon cancer cell LoVo in nude mice was determined according to the model construction (tumor cells were inoculated at $2 \times 10^6/0.1$ ml/mouse) and administration methods of Example 3. There were 6 groups in the experiment, including diluted buffer solution group as vehicle control (20 mM sodium citrate, 0.3% sodium chloride, 5% trehalose, 0.05% Tween 80, pH 6), Erbitux monoclonal antibody group (3 mg/kg), MYK-3 groups (three doses: 0.3 mg/kg, 1 mg/kg, 3 mg/kg), and non-binding control ADC group (3 mg/kg), wherein the non-binding control ADC represented non-binding ADC control (which was anti-CD20 mAb-vcMMAE) with the same loading, and this conjugate was prepared by the same method as MYK-3. The experimental results were shown in FIG. 10.

It can be seen from the figure that MYK-3 at dose of 3 mg/kg exhibits complete inhibition on the growth of LoVo cell tumors, and MYK-3 at dose of 1 mg/kg shows more potent activity in comparison to the marketed Erbitux at dose of 3 mg/kg.

Example 6: Comparison of Inhibition Activity on Cells In Vitro Between MYK-3 and BA03-MC-MMAE, BA03-MCC-MMAE The structures of MC-MMAE and MCC-MMAE are shown as follows:

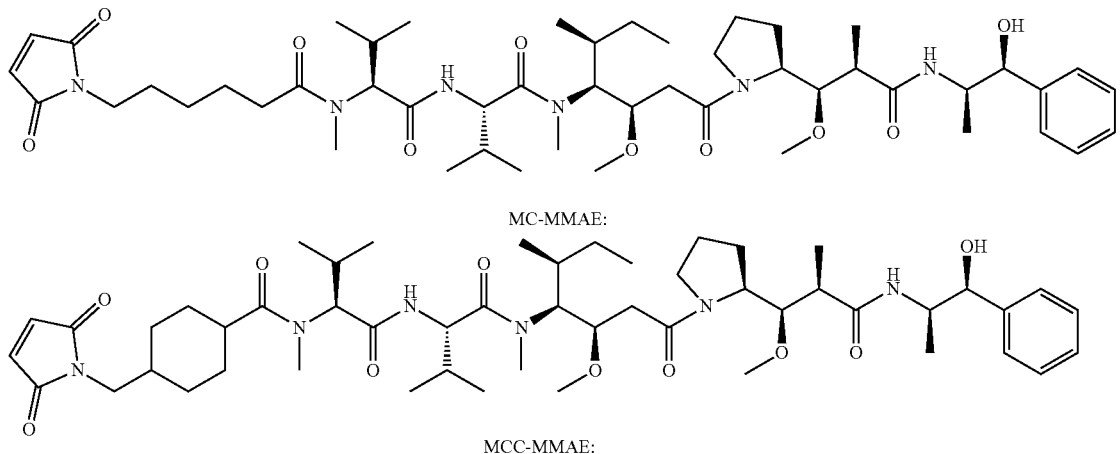

MC-MMAE:

MCC-MMAE:

It can be seen from the figure that monoclonal antibody BA03 showed a certain inhibitory activity on the growth of colorectal cancer cell DiFi with EGFR overexpression; and there was not significant difference in the activity between the BA03 plus free vcMMAE in an amount equivalent to the loading mole number of MYK-3 and BA03 alone. However, MYK-3 as an ADC molecule that was formed by conjugating BA03 with vcMMAE showed an inhibitory activity on growth of DiFi colorectal cancer cells much higher than those of monoclonal antibody BA03 itself and BA03 plus free vcMMAE in an amount equivalent to the loading mole number of MYK-3, and EC50 values were elevated by about 8 times.

MC-MMAE and MCC-MMAE were prepared by referring to the method of Example 1.

Figure 11:
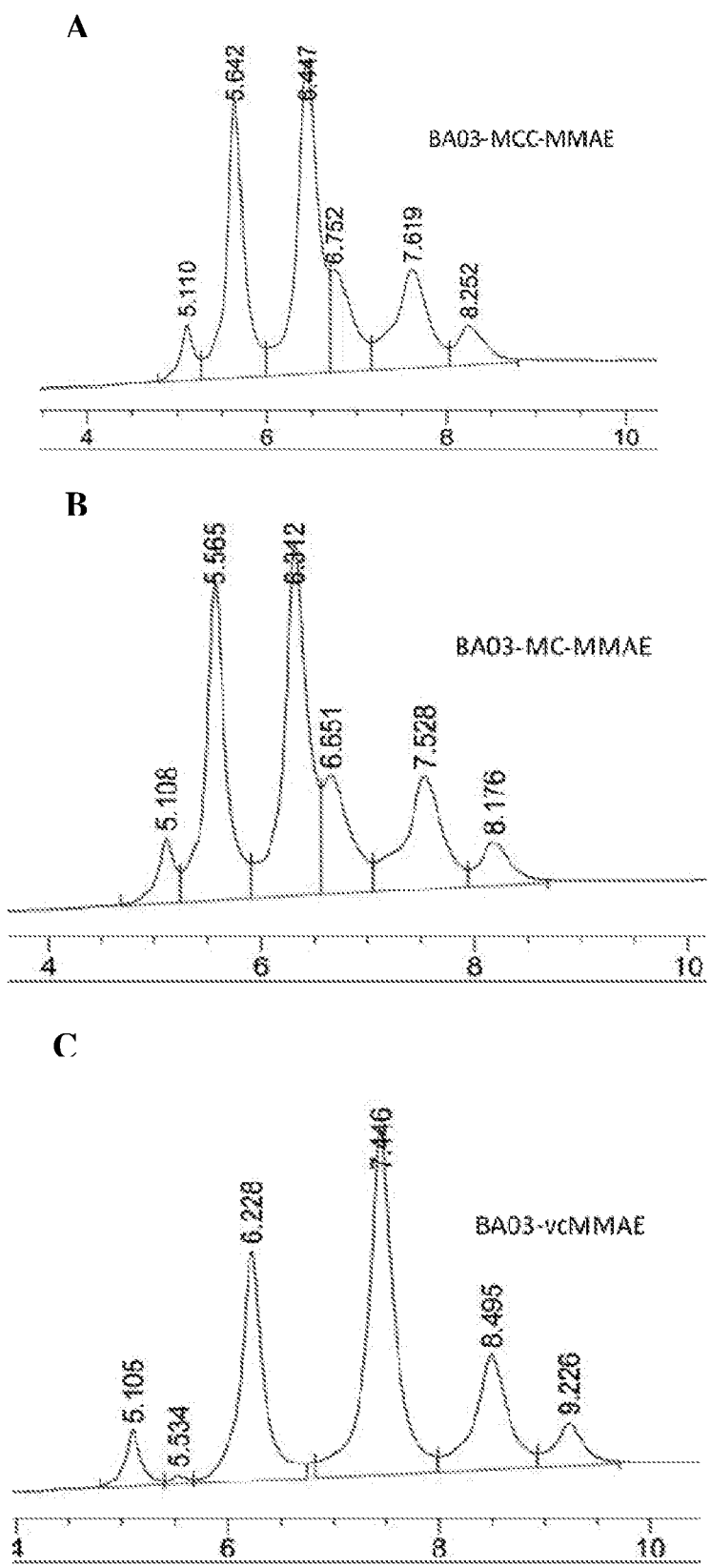
FIG. 11 shows HIC-HPLC analysis diagrams of BA03-MCC-MMAE, BA03-MC-MMAE and MYK-3.

Determination of drug/antibody ratio: HIC-HPLC assay was used for determination of drug/antibody ratio, and specific method could be seen in Example 1. The measured drug/antibody ratios for MYK-3 (i.e., BA03-vcMMAE), BA03-MC-MMAE and BA03-MCC-MMAE were all of 3.9, see also FIG. 11.

Figure 12:
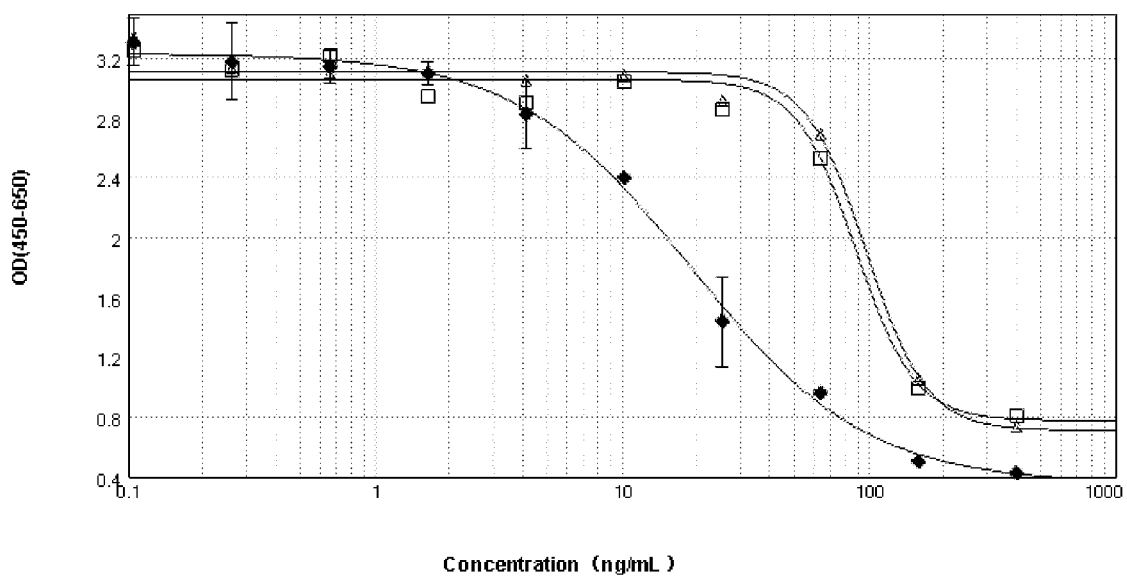
FIG. 12 shows comparison of in vitro cell activities of MYK-3 with BA03-MC-MMAE, BA03-MCC-MMAE, wherein □ represents BA03-MC-MMAE, ◇ represents BA03-MCC-MMAE, and ♦ represents MYK-3.

The method for detecting inhibition activity on cells in vitro can refer to Example 2. In short, a number of DiFi cells were taken, inoculated in 96-well plates, cultured for 24 hours, then three samples BA03-MC-MMAE, BA03-MCC-MMAE, MYK-3 in different concentrations of a serial dilution were added. After further incubation for 96 hours, CCK-8 reagent was added for color development, the OD value of each well of the 96-well plates was read by a microplate reader, the number of viable cells in samples of different concentrations was measured, and the inhibitory effect of the samples on the proliferation of DiFi cell lines was determined. The experimental results were shown in FIG. 12, in which the EC50 values of BA03-MC-MMAE, BA03-MCC-MMAE and MYK-3 were 72.6 ng/mL, 71.6 ng/mL and 9.8 ng/mL, respectively.

It can be seen from the figure that the cell proliferation inhibitory activity of MYK-3 is significantly higher than those of BA03-MC-MMAE and BA03-MCC-MMAE. In fact, the cell proliferation inhibitory activities of BA03-MC-MMAE and BA03-MCC-MMAE were similar to the activity of monoclonal antibody BA03 itself. This shows that when the same monoclonal antibody and cytotoxic small molecules are used, the use of different linkers may cause significant differences in ADC activity.

While specific embodiments of the present invention have been described in detail, those skilled in the art will understand that various modifications and substitutions can be made to those details according to all teachings that have been disclosed, and all of these changes fall within the scope of the present invention. The full scope of the invention is given by the appended claims and any equivalents thereof.

What is claimed is:

1. An antibody-drug conjugate or a pharmaceutically acceptable salt thereof, comprising an anti-epidermal growth factor receptor antibody covalently linked to a cytotoxic agent via a cleavable linker, wherein the anti-epidermal growth factor receptor antibody comprises a heavy chain and a light chain, wherein the heavy chain has a variable region comprising CDR1, CDR2 and CDR3 having sequences as shown in SEQ ID NOs: 5 to 7, and the light chain has a variable region comprising CDR1, CDR2 and CDR3 having sequences as shown in SEQ ID NOs: 12 to 14.

2. The antibody-drug conjugate or the pharmaceutically acceptable salt thereof according to claim 1, wherein FR1, FR2, FR3, FR4 of the variable region of the heavy chain of the anti-epidermal growth factor receptor antibody respectively comprise sequences as shown in SEQ ID NOs: 8 to 11.

3. The antibody-drug conjugate or the pharmaceutically acceptable salt thereof according to claim 1, wherein FR1, FR2, FR3, FR4 of the variable region of the light chain of the anti-epidermal growth factor receptor antibody respectively comprise sequences as shown in SEQ ID NOs: 15 to 18.

4. The antibody-drug conjugate or the pharmaceutically acceptable salt thereof according to claim 1, wherein the heavy chain of the anti-epidermal growth factor receptor antibody has a constant region selected from the group consisting of a human IgG constant region, a human IgM constant region, a human IgA constant region, and a human IgD constant region.

5. The antibody-drug conjugate or the pharmaceutically acceptable salt thereof according to claim 4, wherein the IgG is selected from the group consisting of IgG1, IgG2, IgG3 and IgG4.

6. The antibody-drug conjugate or the pharmaceutically acceptable salt thereof according to claim 4, wherein the constant region of the heavy chain of the anti-epidermal growth factor receptor antibody comprises an amino acid sequence as shown in SEQ ID NO: 3.

7. The antibody-drug conjugate or the pharmaceutically acceptable salt thereof according to claim 1, wherein the light chain of the anti-epidermal growth factor receptor antibody has a constant region selected from the group consisting of a human lambda constant region, and a human kappa constant region.

8. The antibody-drug conjugate or the pharmaceutically acceptable salt thereof according to claim 7, wherein the constant region of the light chain of the anti-epidermal growth factor receptor antibody comprises an amino acid sequence as shown in SEQ ID NO: 4.

9. The antibody-drug conjugate or the pharmaceutically acceptable salt thereof according to claim 1, which has a structure as shown in Formula I, Ab-(L-D)$_p$    Formula I wherein:
Ab represents the anti-epidermal growth factor receptor antibody;
L represents a cleavable linker;
D represents the cytotoxic agent;
p represents 1-9.

10. The antibody-drug conjugate or the pharmaceutically acceptable salt thereof according to claim 9, wherein the cytotoxic agent is selected from the group consisting of chemotherapeutic agents, radioisotopes, antibiotics, enzymes, and biologically active peptides.

11. The antibody-drug conjugate or the pharmaceutically acceptable salt thereof according to claim 10, wherein the cytotoxic agent is selected from the group consisting of Monomethyl auristatin E (MMAE), Monomethyl auristatin F (MMAF), maytansinoid alkaloids, Calicheamicin, duocarmycin MGBA, doxorubicin, ricin, diphtheria toxin, I131, and tumor necrosis factors.

12. The antibody-drug conjugate or the pharmaceutically acceptable salt thereof according to claim 9, wherein the linker is selected from the group consisting of valine-citrulline (val-cit), alanine-phenylalanine (ala-phe), N-succinimidyl 4-(2-pyridylthio)valerate (SPP), and 6-maleimidocaproyl-valine-citrulline-p-aminobenzyloxycarbonyl (MC-vc-PAB).

13. The antibody-drug conjugate or the pharmaceutically acceptable salt thereof according to claim 9, which is:

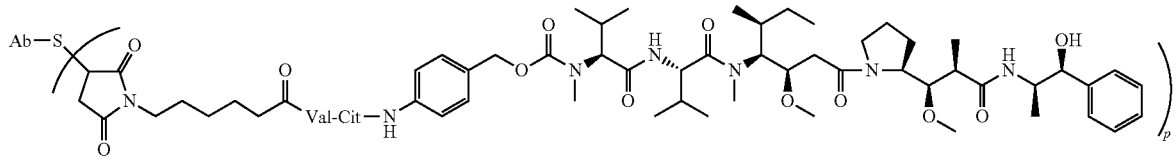

wherein Ab represents the anti-epidermal growth factor receptor antibody, p is 1-8.

14. The antibody-drug conjugate or the pharmaceutically acceptable salt thereof according to claim 9, wherein the linker is 6-maleimidocaproyl-valine-citrulline-p-aminobenzyloxycarbonyl (MC-vc-PAB).

15. A composition, which comprises the antibody-drug conjugate or the pharmaceutically acceptable salt thereof according to claim 1, optionally, further comprises at least one pharmaceutically acceptable carrier, diluent or excipient.

16. A method for treatment of a disease associated with epidermal growth factor receptor (EGFR), comprising: administering to a subject in need a therapeutically effective amount of the antibody-drug conjugate or the pharmaceutically acceptable salt thereof according to claim 1.

17. The method according to claim 16, wherein the disease associated with epidermal growth factor receptor (EGFR) is a tumor associated with overexpression of EGFR.

18. A method for inhibiting tumor angiogenesis, delaying tumor progression, inhibiting tumor growth, or inhibiting tumor cell proliferation, comprising: administering to a subject in need a therapeutically effective amount of the antibody-drug conjugate or the pharmaceutically acceptable salt thereof according to claim 1.

19. The method according to claim 18, wherein the tumor is selected from colon cancer, rectal cancer, head and neck cancer, lung cancer, ovarian cancer, cervical cancer, bladder cancer, esophageal cancer, breast cancer, renal cancer, prostate cancer, gastric cancer, pancreatic cancer and brain glioma.

20. The method according to claim 17, wherein the tumor is a tumor with KRAS gene mutation.

21. The method according to claim 17, wherein the tumor is a tumor with BRAF gene mutation.

22. The method according to claim 19, wherein the tumor is a tumor with KRAS gene mutation.

23. The method according to claim 19, wherein the tumor is a tumor with BRAF gene mutation.

* * * * *

SEQUENCE LISTING

<160> NUMBER OF SEQ ID NOS: 18

<210> SEQ ID NO 1
<211> LENGTH: 119
<212> TYPE: PRT
<213> ORGANISM: Artificial
<220> FEATURE:
<223> OTHER INFORMATION: sequence of variable region of heavy chain

<400> SEQUENCE: 1

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser Asn Tyr
            20                  25                  30

Asp Val His Trp Val Arg Gln Ala Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Ala Leu Asp Tyr Tyr Asp Tyr Glu Phe Ala Tyr Trp Gly Gln Gly
            100                 105                 110

Thr Leu Val Thr Val Ser Ser
        115
```

<210> SEQ ID NO 2
<211> LENGTH: 107
<212> TYPE: PRT
<213> ORGANISM: Artificial
<220> FEATURE:
<223> OTHER INFORMATION: sequence of variable region of light chain

<400> SEQUENCE: 2

```
Glu Ile Val Leu Thr Gln Ser Pro Asp Phe Gln Ser Val Thr Pro Lys
1               5                   10                  15

Glu Lys Val Thr Ile Thr Cys Arg Ala Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Asn Asn Glu Trp Pro Thr
```

```
                        85                  90                  95
Ser Phe Gly Gln Gly Thr Lys Leu Glu Ile Lys
            100                 105
```

<210> SEQ ID NO 3
<211> LENGTH: 330
<212> TYPE: PRT
<213> ORGANISM: Artificial
<220> FEATURE:
<223> OTHER INFORMATION: sequence of constant region of heavy chain

<400> SEQUENCE: 3

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 4
<211> LENGTH: 107
<212> TYPE: PRT
<213> ORGANISM: Artificial
<220> FEATURE:
<223> OTHER INFORMATION: sequence of constant region of light chain

<400> SEQUENCE: 4

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 5
<211> LENGTH: 5
<212> TYPE: PRT
<213> ORGANISM: Artificial
<220> FEATURE:
<223> OTHER INFORMATION: HCDR1

<400> SEQUENCE: 5

Asn Tyr Asp Val His
1               5

<210> SEQ ID NO 6
<211> LENGTH: 16
<212> TYPE: PRT
<213> ORGANISM: Artificial
<220> FEATURE:
<223> OTHER INFORMATION: HCDR2

<400> SEQUENCE: 6

Val Ile Trp Ser Gly Gly Asn Thr Asp Tyr Asn Thr Pro Phe Thr Ser
1               5                   10                  15

<210> SEQ ID NO 7
<211> LENGTH: 11
<212> TYPE: PRT
<213> ORGANISM: Artificial
<220> FEATURE:
<223> OTHER INFORMATION: HCDR3

<400> SEQUENCE: 7

Ala Leu Asp Tyr Tyr Asp Tyr Glu Phe Ala Tyr
1               5                   10

<210> SEQ ID NO 8
<211> LENGTH: 30
<212> TYPE: PRT
<213> ORGANISM: Artificial
<220> FEATURE:
<223> OTHER INFORMATION: FR1 of VH

<400> SEQUENCE: 8
```

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Ser
            20                  25                  30
```

<210> SEQ ID NO 9
<211> LENGTH: 14
<212> TYPE: PRT
<213> ORGANISM: Artificial
<220> FEATURE:
<223> OTHER INFORMATION: FR2 of VH

<400> SEQUENCE: 9

```
Trp Val Arg Gln Ala Pro Gly Lys Gly Leu Glu Trp Leu Gly
1               5                   10
```

<210> SEQ ID NO 10
<211> LENGTH: 32
<212> TYPE: PRT
<213> ORGANISM: Artificial
<220> FEATURE:
<223> OTHER INFORMATION: FR3 of VH

<400> SEQUENCE: 10

```
Arg Leu Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30
```

<210> SEQ ID NO 11
<211> LENGTH: 11
<212> TYPE: PRT
<213> ORGANISM: Artificial
<220> FEATURE:
<223> OTHER INFORMATION: FR4 of VH

<400> SEQUENCE: 11

```
Trp Gly Gln Gly Thr Leu Val Thr Val Ser Ser
1               5                   10
```

<210> SEQ ID NO 12
<211> LENGTH: 11
<212> TYPE: PRT
<213> ORGANISM: Artificial
<220> FEATURE:
<223> OTHER INFORMATION: LCDR1

<400> SEQUENCE: 12

```
Arg Ala Ser Gln Ser Ile Gly Thr Asn Ile His
1               5                   10
```

<210> SEQ ID NO 13
<211> LENGTH: 7
<212> TYPE: PRT
<213> ORGANISM: Artificial
<220> FEATURE:
<223> OTHER INFORMATION: LCDR2

<400> SEQUENCE: 13

```
Tyr Ala Ser Glu Ser Ile Ser
1               5
```

<210> SEQ ID NO 14
<211> LENGTH: 10
<212> TYPE: PRT
<213> ORGANISM: Artificial

<220> FEATURE:
<223> OTHER INFORMATION: LCDR3

<400> SEQUENCE: 14

Gln Gln Asn Asn Glu Trp Pro Thr Ser Phe
1               5                   10

<210> SEQ ID NO 15
<211> LENGTH: 23
<212> TYPE: PRT
<213> ORGANISM: Artificial
<220> FEATURE:
<223> OTHER INFORMATION: FR1 of VL

<400> SEQUENCE: 15

Glu Ile Val Leu Thr Gln Ser Pro Asp Phe Gln Ser Val Thr Pro Lys
1               5                   10                  15

Glu Lys Val Thr Ile Thr Cys
            20

<210> SEQ ID NO 16
<211> LENGTH: 15
<212> TYPE: PRT
<213> ORGANISM: Artificial
<220> FEATURE:
<223> OTHER INFORMATION: FR2 of VL

<400> SEQUENCE: 16

Trp Tyr Gln Gln Lys Pro Asp Gln Ser Pro Lys Leu Leu Ile Lys
1               5                   10                  15

<210> SEQ ID NO 17
<211> LENGTH: 32
<212> TYPE: PRT
<213> ORGANISM: Artificial
<220> FEATURE:
<223> OTHER INFORMATION: FR3 of VL

<400> SEQUENCE: 17

Gly Ile Pro Ser Arg Phe Ser Gly Ser Gly Ser Gly Thr Asp Phe Thr
1               5                   10                  15

Leu Thr Ile Asn Ser Leu Glu Ala Glu Asp Ala Ala Thr Tyr Tyr Cys
            20                  25                  30

<210> SEQ ID NO 18
<211> LENGTH: 9
<212> TYPE: PRT
<213> ORGANISM: Artificial
<220> FEATURE:
<223> OTHER INFORMATION: FR4 of VL

<400> SEQUENCE: 18

Gly Gln Gly Thr Lys Leu Glu Ile Lys
1               5